(12) United States Patent
Luan et al.

(10) Patent No.: US 12,391,706 B2
(45) Date of Patent: Aug. 19, 2025

(54) MULTI-TARGET TYROSINE KINASE INHIBITOR

(71) Applicant: SHENZHEN NEPTUNUS PHARMACEUTICAL RESEARCH INSTITUTE CO., LTD., Shenzhen (CN)

(72) Inventors: Shenglin Luan, Shenzhen (CN); Tian Tang, Shenzhen (CN); Hanmin Huang, Shenzhen (CN); Jing Wu, Shenzhen (CN); Yidong Feng, Shenzhen (CN); Tao Shi, Shenzhen (CN); Hanlin Feng, Shenzhen (CN); Lin Yu, Shenzhen (CN)

(73) Assignee: SHENZHEN NEPTUNUS PHARMACEUTICAL RESEARCH INSTITUTE CO., LTD., Shenzhen (CN)

( * ) Notice: Subject to any disclaimer, the term of this patent is extended or adjusted under 35 U.S.C. 154(b) by 605 days.

(21) Appl. No.: 17/795,516

(22) PCT Filed: Feb. 2, 2021

(86) PCT No.: PCT/CN2021/074809
§ 371 (c)(1),
(2) Date: Jul. 26, 2022

(87) PCT Pub. No.: WO2021/164538
PCT Pub. Date: Aug. 26, 2021

(65) Prior Publication Data
US 2023/0102146 A1 Mar. 30, 2023

(30) Foreign Application Priority Data

Feb. 18, 2020 (CN) .......................... 202010099747.2

(51) Int. Cl.
| C07D 495/04 | (2006.01) |
| A61K 31/4365 | (2006.01) |
| A61P 35/00 | (2006.01) |
| C07F 9/6561 | (2006.01) |

(52) U.S. Cl.
CPC ........ C07D 495/04 (2013.01); A61K 31/4365 (2013.01); A61P 35/00 (2018.01); C07F 9/6561 (2013.01)

(58) Field of Classification Search
CPC .............. C07D 495/04; A61K 31/4365; A61K 31/496; A61K 31/5377; A61P 35/00; A61P 35/02; C07F 9/6561
See application file for complete search history.

(56) References Cited

FOREIGN PATENT DOCUMENTS

| CN | 101796055 A | 8/2010 |
| CN | 108530464 | 9/2018 |
| CN | 108530464 A | 9/2018 |
| CN | 109384799 | 2/2019 |
| WO | 2008041053 | 4/2008 |
| WO | WO-2018157737 A1 * | 9/2018 ......... A61K 31/4365 |

OTHER PUBLICATIONS

Chinese Office Action dated Apr. 12, 2022 for Chinese Application No. 202010099747.2.
Chinese Office Action dated Mar. 24, 2022 for Chinese Application No. 202010099747.2.
European Search Report dated Feb. 9, 2024 for European Patent Application No. 21757014.2-111.
Dhareshwar, S., et al., "Prodrugs of Alcohols and Phenols", Department of Pharmaceutical Chemistry.

* cited by examiner

Primary Examiner — Joseph K McKane
Assistant Examiner — Meghan C Heasley
(74) Attorney, Agent, or Firm — Gregory P. Einhorn; Greer, Burns & Crain, Ltd.

(57) ABSTRACT

The present invention relates to a multi-target tyrosine kinase inhibitor, which is a compound having protein kinase inhibitory activity as shown in formula (I). The compound is metabolized into an active small molecule td32-4 that inhibits tumor growth in vivo, so as to achieve the anti-tumor effect. Compared with td32-4, the compound of the present invention has significantly improved solubility and oral bioavailability, and shows strong anti-tumor activity in animal in vivo experiments. The present invention relates to a synthetic method for the compound of formula (I) and an application thereof in the field of pharmaceuticals.

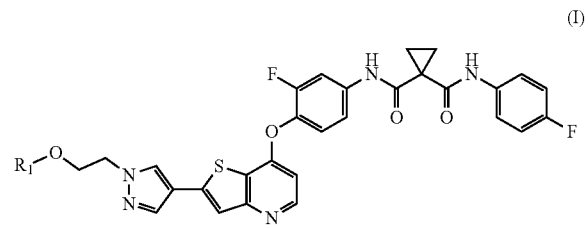

(I)

13 Claims, 6 Drawing Sheets

*NA: The animal tumor could not be dissected and seperated since the tumor was scratched due to movement.

MULTI-TARGET TYROSINE KINASE INHIBITOR

RELATED APPLICATIONS

This application is a national phase application claiming benefit of priority under 35 U.S.C. § 371 to International (PCT) Patent Application serial number PCT/CN2021/074809, filed Feb. 2, 2021, which claims benefit of priority to Chinese Patent Application No. CN 202010099747.2, filed Feb. 18, 2020. The aforementioned applications are expressly incorporated herein by reference in their entirety and for all purposes.

FIELD OF THE INVENTION

The present invention belongs to the technical field of medicine, in particular to a multi-target tyrosine kinase inhibitor having 2-substituted pyrazolylpyrido[3,2-b]thiophene as the core and its application in the field of medicine.

BACKGROUND OF THE INVENTION

Many important life activities in cells are closely related to phosphorylation of proteins, such as cell proliferation, differentiation and apoptosis. Activity abnormalities of protein kinases are widely present in tumor cells. With the advancement of medical technology, more and more protein kinases have become effective drug targets, and kinase inhibitor drugs have become an indispensable strategy in the field of tumor targeted therapy.

The receptor tyrosine kinase c-Met is the only known receptor for hepatocyte growth factor (HGF), and the HGF/c-Met pathway plays an important role in embryogenesis. Expression abnormalities of HGF and c-Met have been found in various tumors. Excessive activation of c-Met can promote the growth and survival of tumor cells, the generation of new blood vessels, and the invasion and metastasis.

Clinically, expression abnormalities of HGF and/or Met have been found in many different tumors, including glioma, melanoma, hepatocellular carcinoma, lung cancer, pancreatic cancer, prostate cancer, ovarian cancer, breast cancer, gastric cancer, renal cell carcinoma, etc., and are often accompanied by a poor prognosis.

The generation of new blood vessels is considered to be an important step in tumorigenesis and cancer development. At present, there are many drugs targeting the angiogenesis factor VEGF or its receptor VEGFR, which can inhibit tumor growth by inhibiting the angiogenesis of tumor cells. For example, the drugs such as bevacizumab, sunitinib, sorafenib all have the above pharmacological effects. However, it is clinically found that the anti-cancer effect of such drugs decreased significantly after several weeks of efficacy. Mechanistic studies have found that hypoxia-inducible factor HIF-α induces the high expression of Met, which leads to the body's resistance to the inhibition of VEGF/VEGFR pathway. Recent studies have shown that some VEGFR inhibitors, such as sunitinib, as well as VEGF monoclonal antibodies, can increase the invasive and migratory capacity of tumor cells, and the tumor cells are accompanied by higher levels of Met expression. Therefore, simultaneous inhibition of VEGFR and c-Met may have better tumor inhibition, and also reduce the invasion and metastasis of tumor cells.

C-kit kinase is also an important anti-tumor therapeutic target, and c-kit activating mutations are present in approximately 80% of gastrointestinal stromal tumors (GISTs). Mutations in c-kit are also associated with melanoma, systemic mastocytosis, and acute myeloid leukemia.

Chinese patent application CN108530464A relates to a new compound td32-4 (N-3-fluoro-4-((2-(1-(2-hydroxyethyl)-1H-pyrazol-4-yl)thieno[3,2-b]pyridin-7-yl)oxy)phenyl)-N-(4-fluorophenyl) cyclopropane-1,1-dicarboxamide), which exhibits potent inhibitory activity against the three targets of VEGFR/c-Met/c-Kit, as well as potent anti-proliferative activity in multiple tumor cell models. It shows good oral bioavailability (F=71.6%) at low dose (10 mg·kg$^{-1}$). Although the compound exhibits good biological activity, the extremely poor solubility of td32-4 limits the further development of this compound as a good targeted anti-tumor drug. This is mainly reflected in the following aspects: 1) The compound has extremely poor water solubility. It can be administered in the form of solution at small doses, which can achieve better absorption, but when the therapeutic dose is increased (>60 mg·kg$^{-1}$), it is administered in the form of solid preparation/suspension solution, the drug cannot be effectively released in the animal/human body, the blood drug concentration is extremely low, and the oral bioavailability is very poor (F=3%~15%); 2) The absorption of a poorly soluble drug varies greatly among individuals, and there are great risks and difficulties in the preclinical/clinical safety evaluation of the drug; 3) There is a phenomenon of absorption saturation when the drug is administered in large doses. No matter how the dose is increased, the blood drug concentration still cannot be increased.

In order to solve the above problems, the present invention has carried out structural modifications on td32-4, and proposes a series of compounds represented by the following formula (I), which can not only solve the solubility problem of td32-4, but also maintain its potent anti-tumor activity in vivo, and are expected to be developed into a new generation of VEGFR/c-Met/c-Kit multi-target kinase inhibitor drugs.

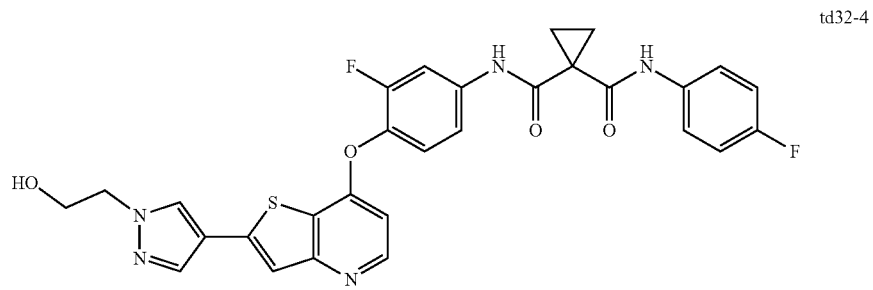 [SMILES: O=C(Nc1ccc(F)cc1)C1(C(=O)Nc2ccc(Oc3ccnc4cc(-c5cnn(CCO)c5)sc34)c(F)c2)CC1]

td32-4

SUMMARY OF THE INVENTION

The present invention relates to a compound or a pharmaceutically acceptable salt, isomer and racemate thereof, wherein the compound has the structure represented by the general formula (I):

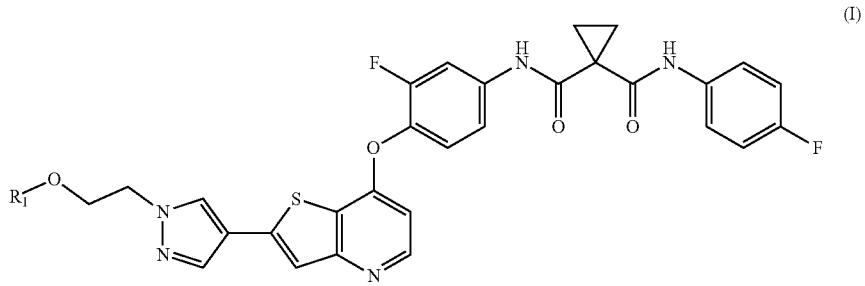

wherein,

R1 is optionally selected from the following substituents: carboxyl-substituted C3~C8 alkyl acyl, substituted or unsubstituted phosphonyl,

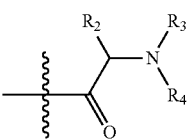 and 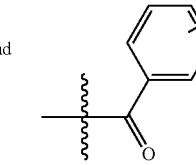

R2 is optionally selected from the following groups: hydrogen, halogen, R5-substituted C1~C8 alkyl and R5-substituted C6~C12 aryl;

R3, R4 are optionally selected from the following groups: hydrogen and R5-substituted C1~C6 alkyl, or R3 and R4 constitute a five- to twelve-membered aliphatic heterocycle;

R5 is optionally selected from the following groups: hydrogen, 1~3 halogens, hydroxyl, C1~C6 alkoxy and C6~C12 aryl;

further, R1 may be selected from 3-carboxypropionyl, 4-carboxybutanoyl, 5-carboxypentanoyl, 6-carboxyhexanoyl, and

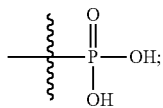 [SMILES: *P(=O)(O)O]

even further, when $R_1 =$

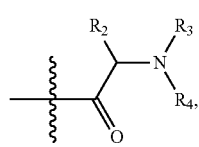

R2 is optionally selected from the following groups: hydrogen, halogen, R5-substituted C1~C8 alkyl and R5-substituted C6~C12 aryl;

R3, R4 are optionally selected from the following groups: hydrogen and R5-substituted C1~C6 alkyl, or R3 and R4 constitute a five- to twelve-membered aliphatic heterocycle;

R5 is optionally selected from the following groups: hydrogen, 1~3 halogens, hydroxyl, C1~C6 alkoxy and C6~C12 aryl.

further, when R1=

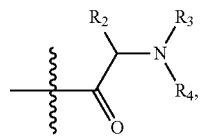

R2 is optionally selected from the following groups: hydrogen, fluorine, chlorine, bromine, methyl, —CH2F, —CHF2, —CF3, ethyl, propyl, isopropyl, cyclopropyl, butyl, isobutyl, benzyl, 4-hydroxybenzyl, phenyl and 4-fluorophenyl;

R3, R4 are optionally selected from the following groups: hydrogen, methyl, ethyl, 2,2-dimethoxyethyl, propyl and butyl, or R3 and R4 constitute morpholine, pyridine, pyrrole, piperidine, piperidinylpiperidine or N-methyl piperidine;

further, when R1=

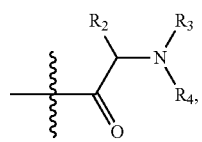

R2 is selected from the following groups: hydrogen, methyl, —CH2F, —CHF2, —CF3, ethyl, propyl, isopropyl, isobutyl, benzyl, 4-hydroxybenzyl and phenyl;

R3, R4 are optionally selected from the following groups: hydrogen, methyl, ethyl, and 2,2-dimethoxyethyl, or R3 and R4 constitute morpholine or N-methylpiperidine;

when R1=

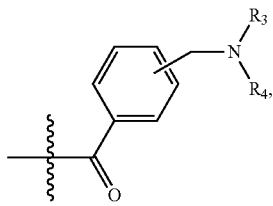

R3, R4 are optionally selected from the following groups: hydrogen, methyl, ethyl, 2,2-dimethoxyethyl, propyl and butyl, or R3 and R4 constitute morpholine, pyridine, pyrrole, piperidine, piperidinylpiperidine, or N-methylpiperidine.

In particular embodiments of the present invention, preferred compounds of the formula I are as follows:

| | Structural formula | Chemical formula |
|---|---|---|
| 1 | | $C_{33}H_{27}F_2N_5O_7S$ |
| 2 | | $C_{29}H_{24}F_2N_5O_7PS$ |
| 3 | | $C_{33}H_{30}F_2N_6O_5S$ |
| 4 | | $C_{35}H_{34}F_2N_6O_6S$ |

-continued

| | Structural formula | Chemical formula |
|---|---|---|
| 5 | | $C_{35}H_{32}F_2N_6O_6S$ |
| 6 | | $C_{31}H_{26}F_2N_6O_5S$ |
| 7 | | $C_{32}H_{28}F_2N_6O_5S$ |
| 8 | | $C_{35}H_{34}F_2N_6O_5S$ |
| 9 | | $C_{35}H_{34}F_2N_6O_5S$ |

-continued

| | Structural formula | Chemical formula |
|---|---|---|
| 10 | | $C_{34}H_{32}F_2N_6O_5S$ |
| 11 | | $C_{34}H_{32}F_2N_6O_5S_2$ |
| 12 | | $C_{38}H_{32}F_2N_6O_5S$ |
| 13 | | $C_{34}H_{30}F_2N_6O_5S$ |
| 14 | | $C_{33}H_{29}F_2N_7O_6S$ |

| | Structural formula | Chemical formula |
|---|---|---|
| 15 | 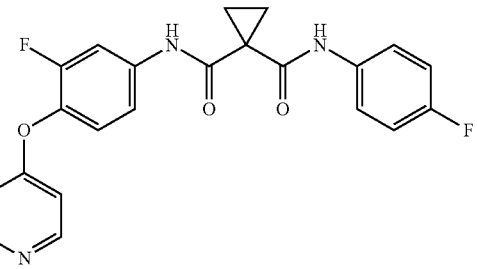 | $C_{34}H_{31}F_2N_7O_6S$ |
| 16 | 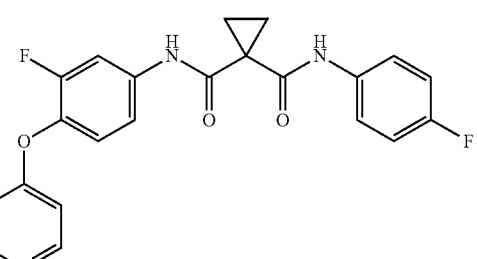 | $C_{40}H_{33}F_2N_7O_5S$ |
| 17 | 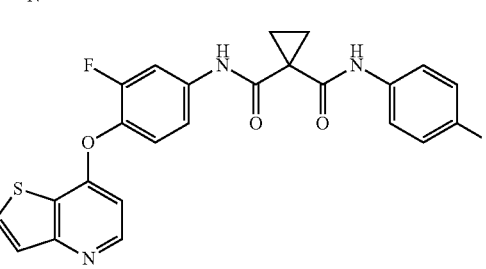 | $C_{35}H_{34}F_2N_6O_7S$ |
| 18 | 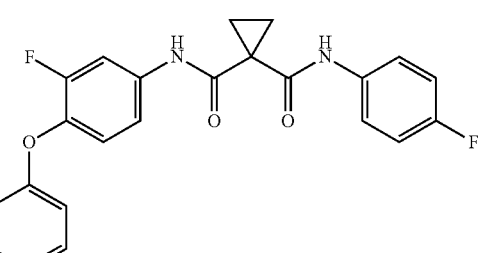 | $C_{34}H_{32}F_2N_6O_5S$ |
| 19 | 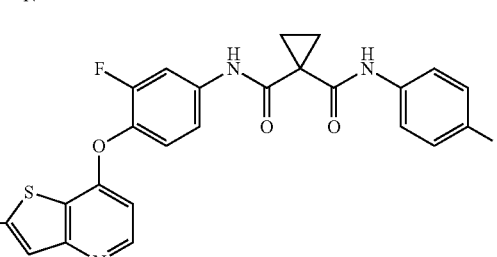 | $C_{41}H_{36}F_2N_6O_6S$ |
| 20 | 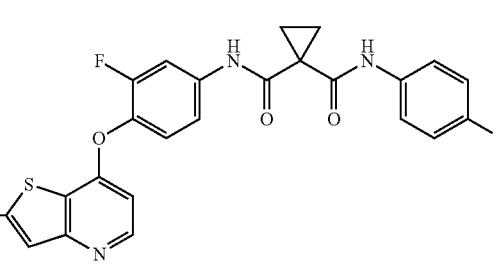 | $C_{41}H_{36}F_2N_6O_6S$ |

| | Structural formula | Chemical formula |
|---|---|---|
| 21 | | $C_{42}H_{39}F_2N_7O_5S$ |
| 22 | | $C_{42}H_{39}F_2N_7O_5S$ |
| 23 | | $C_{41}H_{36}F_2N_6O_5S$ |
| 24 | | $C_{41}H_{36}F_2N_6O_5S$ |

Another object of the present invention is to provide a pharmaceutical composition comprising the compound of the general formula (I) or a pharmaceutically acceptable salt, isomer or racemate thereof as an active ingredient.

Yet another object of the present invention is to provide a use of the compound of the general formula (I) or a pharmaceutically acceptable salt, isomer or racemate thereof in the preparation of a medicament for the treatment of tumors. The tumor comprises: cervical cancer, seminoma, testicular lymphoma, prostate cancer, ovarian cancer, lung cancer, rectal cancer, breast cancer, skin squamous cell carcinoma, colon cancer, liver cancer, pancreatic cancer, stomach cancer, esophageal cancer, thyroid cancer, and/or bladder transitional epithelial cancer, leukemia.

By modifying the structure of td32-4, the compounds provided by the present invention obtain significantly improved solubility, and overcome the existing difficulties such as in pharmacokinetic research, safety evaluation, development of analytical method, preparation/formulation research of td32-4. In addition, due to the extremely poor water solubility of td32-4, it shows extremely poor oral bioavailability in pharmacokinetic studies in rat, limiting the further development of the compound. It has been verified by experiments that the compounds of the present invention can exert pharmacological effects by converting into td32-4 in vivo after oral administration, and show greatly improved oral bioavailability compared with direct oral administration of td32-4, especially when administered at high doses (200 mg·kg$^{-1}$). It has been verified that the compounds of the present invention have potent tumor inhibitory effects when orally administered in animals, while td32-4 has no obvious inhibitory effect on tumors when orally administered at the same dose.

DETAILED DESCRIPTION OF THE INVENTION

Figure 1:
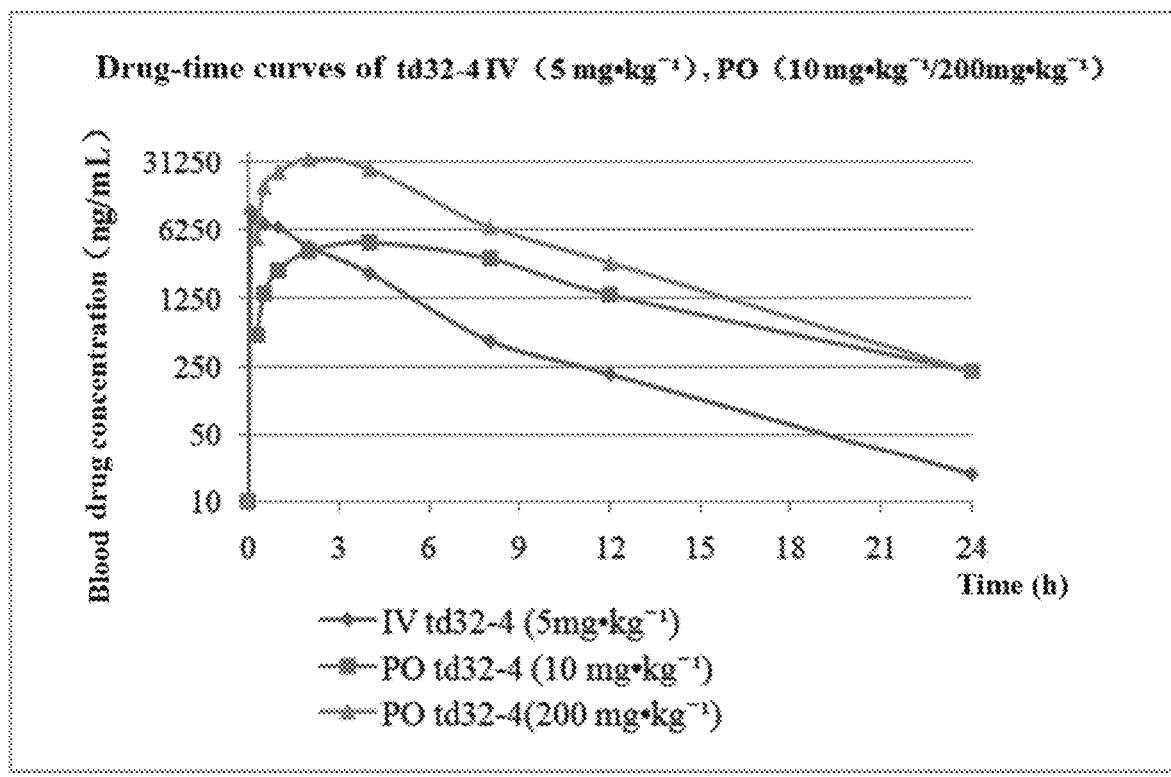
FIG. 1 Blood drug concentration-time curves of td32-4 after intravenous administration at a dose of 5 mg·kg$^{-1}$ and oral administration at a dose of 10 mg·kg$^{-1}$, 200 mg·kg$^{-1}$.

The technical solutions of the present invention will be further described below with reference to some examples. The following examples do not constitute any limitation to the present invention.

The reagents and materials of the present invention are all commercially available products.

Example 1

Synthesis of Compound 4-(2-(4-(7-(2-fluoro-4-(1-((4-fluorophenyl)carbamoyl)cyclopropane-1-carboxamide)phenoxy)thieno[3,2-b]pyridin-2-yl)-1H-pyrazolyl-1-yl)ethoxy)-4-oxobutyric acid (td32-4P1)

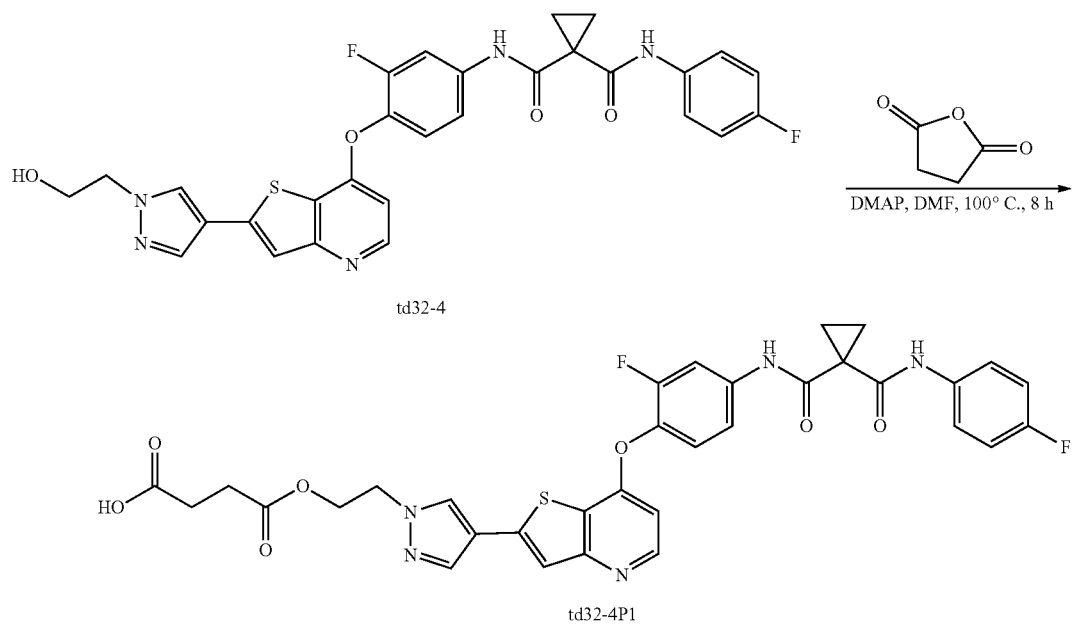

Td32-4 (chemical name: N-3-fluoro-4-((2-(1-(2-hydroxyethyl)-1H-pyrazol-4-yl)thieno[3,2-b]-7-yl)oxy)phenyl)-N-(4-fluorophenyl)cyclopropane-1,1-dicarboxamide) (5 g, 8.7 mmol), 4-DMAP (0.21 g, 1.7 mmol), succinic anhydride (4.34 g, 43.5 mmol) were dissolved in 50 mL of DMF, reacted at 100° C. for 8 hours. The reaction solution was poured into 500 mL of water, stirred to precipitate a solid product, filtered with suction, and the filter cake was washed with 200 mL of water. After the filter cake was dried, the product was gradually dissolved in 20% (w %) sodium carbonate aqueous solution by heating and stirring, and 5% activated carbon was added and refluxed for 1 hour, filtered while hot, and the filtrate was adjusted to pH 1~2 with 2 mol/L dilute hydrochloric acid, to precipitate a large amount of white solid, filtered with suction, and dried in an oven at 55° C. to obtain 4.82 g of white solid. Yield: 82.1%, HPLC purity: 98.0%, LC-MS: 675.4 [M−H]$^-$.

Example 2

Synthesis of Compound 2-(4-(7-(2-fluoro-4-(1-((4-fluorophenyl)carbamoyl)cyclopropane-1-carboxamide)phenoxy)thieno[3,2-b]pyridin-2-yl)-1H-pyrazolyl-1-yl)ethyl phosphate (td32-4P2)

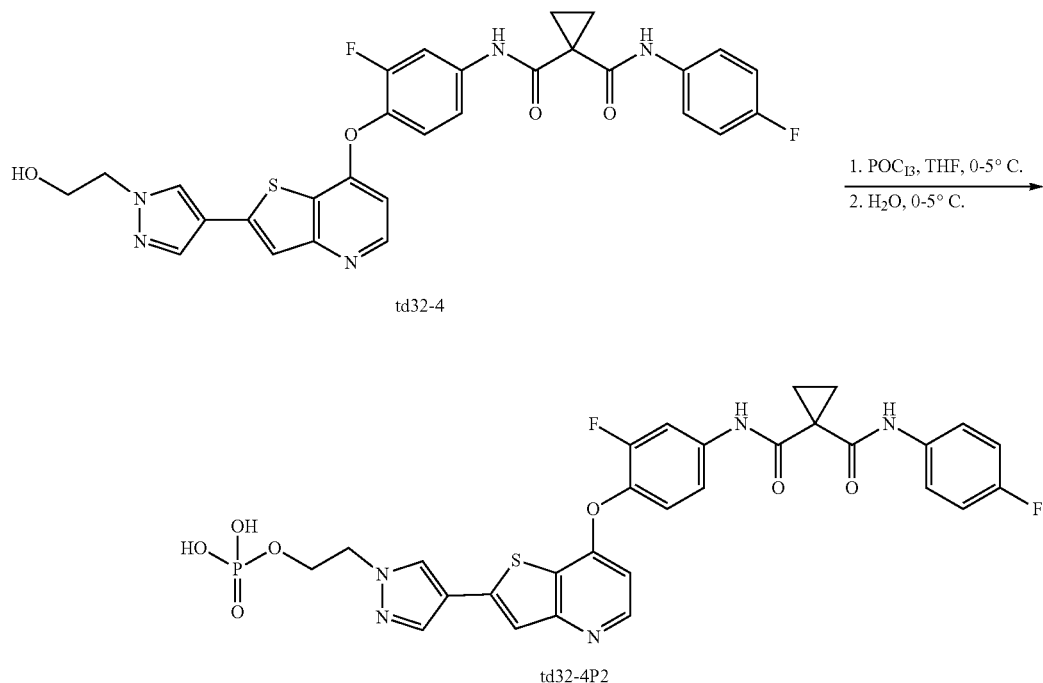

At room temperature, td32-4 (5 g, 8.7 mmol) and triethylamine (1.05 g, 10.4 mmol) were added to 60 mL of tetrahydrofuran, cooled to 0° C., and phosphorus oxychloride in tetrahydrofuran was added dropwise. After the completion of the dropwise addition, the reaction system was stirred for 3 hours at 0~5° C. The above reaction solution was added dropwise to 100 mL of ice water, stirred to precipitate a solid, filtered with suction, and the filter cake was washed with water until the filtrate became neutral, and then dried. After the filter cake was dried, the product was gradually dissolved in 20% (w %) sodium carbonate aqueous solution by heating and stirring, and 5% activated carbon was added and refluxed for 1 hour, filtered while hot, and the filtrate was adjusted to pH 1~2 with 2 mol/L dilute hydrochloric acid, to precipitate a large amount of white solid, filtered with suction, and dried in an oven at 55° C. to obtain 3.56 g of white solid. Yield: 62.5%, HPLC purity: 96.1%, LC-MS: 654.1 [M−H]⁻.

Example 3

Synthesis of Compound 2-(4-(7-(2-fluoro-4-(1-((4-fluorophenyl)carbamoyl)cyclopropane-1-carboxamide)phenoxy)thieno[3,2-b]pyridin-2-yl)-1H-pyrazolyl-1-yl)ethyldimethyl glycinate (td32-4P3)

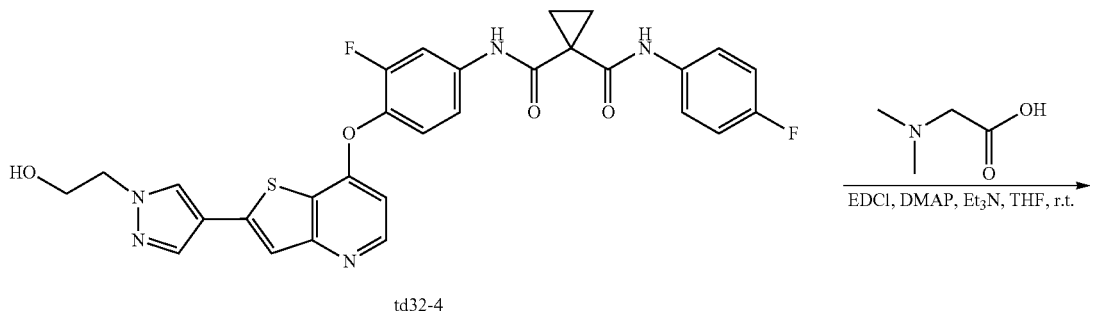

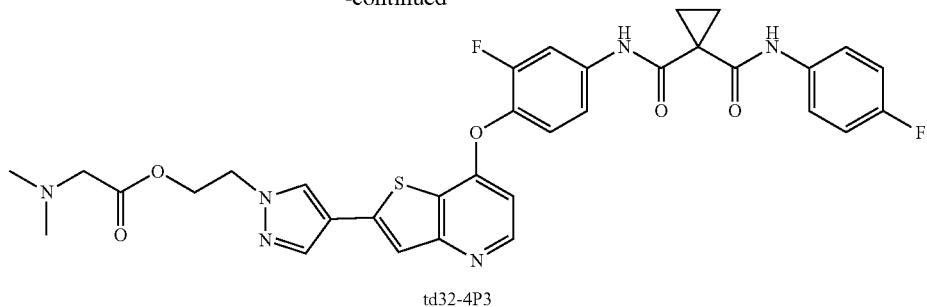

td32-4P3

At 0° C., N,N-dimethylglycine (1.79 g, 17.4 mmol), 1-ethyl-(3-dimethylaminopropyl) carbodiimide hydrochloride (EDCI, 4 g, 20.9 mmol), 4-dimethylaminopyridine (DMAP, 1.59 g, 13.0 mmol) were added to 60 mL of anhydrous tetrahydrofuran, reacted for 30 min, and then td32-4 (5 g, 8.7 mmol) was added to the reaction system, transferred to room temperature and reacted for 24 hours. The reaction solution was filtered, and 200 mL of 1 mol/L dilute hydrochloric acid was added to the filtrate, stirred, and filtered with suction. The filtrate was adjusted to pH 10 with saturated sodium carbonate solution to precipitate a large amount of white solid, and filtered with suction. The filter cake was washed with 100 mL of water, and dried to obtain a crude product.

The crude product was dissolved in 100 mL of 2 mol/L dilute hydrochloric acid, and filtered to remove insoluble materials. The filtrate was adjusted to pH 10 with saturated sodium carbonate to precipitate a large amount of white solid, and filtered with suction. The filter cake was washed with 100 mL of water and then dried. The solid product was dissolved in 80 mL of anhydrous acetone, added with 2 mL of concentrated hydrochloric acid, stirred at room temperature overnight to precipitate a hydrochloride product, and filtered with suction. The filter cake was washed with 50 mL of anhydrous acetone, and dried in an oven at 55° C. to obtain 3.75 g of white solid, yield: 65.3%, HPLC purity: 98.8%, LC-MS: 661.3 [M+H]$^+$.

Example 4

Synthesis of Compound 2-(4-(7-(2-fluoro-4-(1-((4-fluorophenyl)carbamoyl)cyclopropane-1-carboxamide)phenoxy)thieno[3,2-b]pyridin-2-yl)-1H-pyrazolyl-1-yl)ethyldiethyl glycinate (td32-4P4)

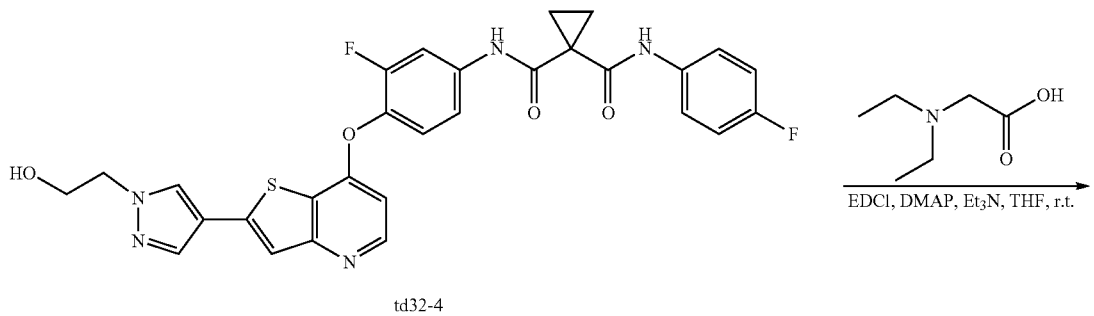

td32-4

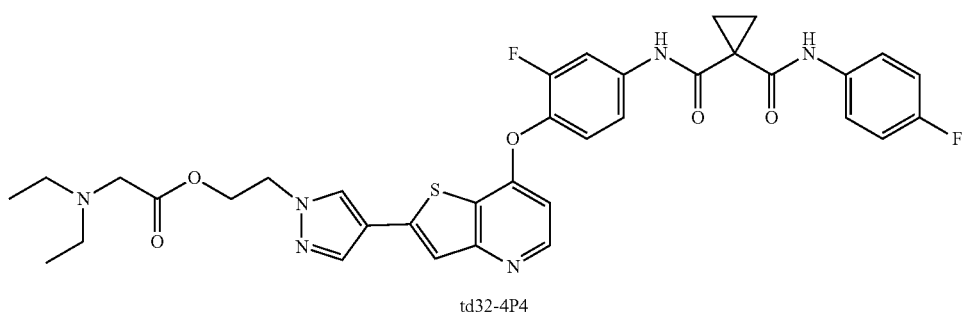

td32-4P4

Using N, N-diethylglycine (2.28 g, 17.4 mmol) and td32-4 (5 g, 8.7 mmol) as raw materials, referring to the synthetic method of Example 3, 4.49 g of white solid was obtained, yield: 75.1%, HPLC purity: 97.9%, LC-MS: 689.3 [M+H]$^+$.

Example 5

Synthesis of Compound 2-(4-(7-(2-fluoro-4-(1-((4-fluorophenyl)carbamoyl)cyclopropane-1-carboxamide)phenoxy)thieno[3,2-b]pyridin-2-yl)-1H-pyrazolyl-1-yl)ethyl 2-morpholine acetate (td32-4P5)

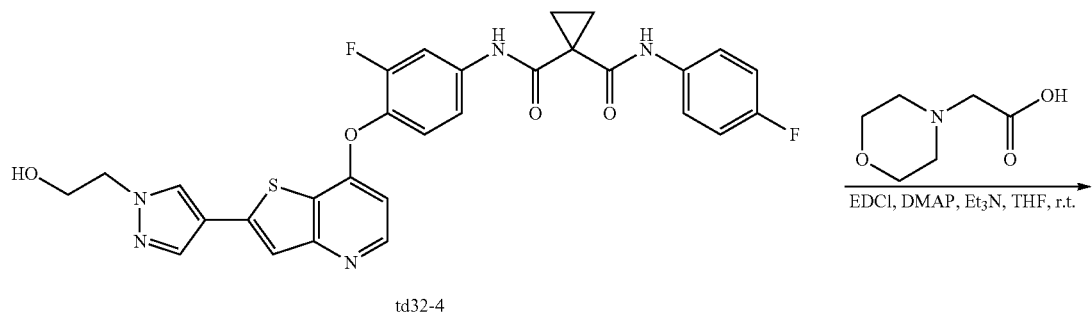

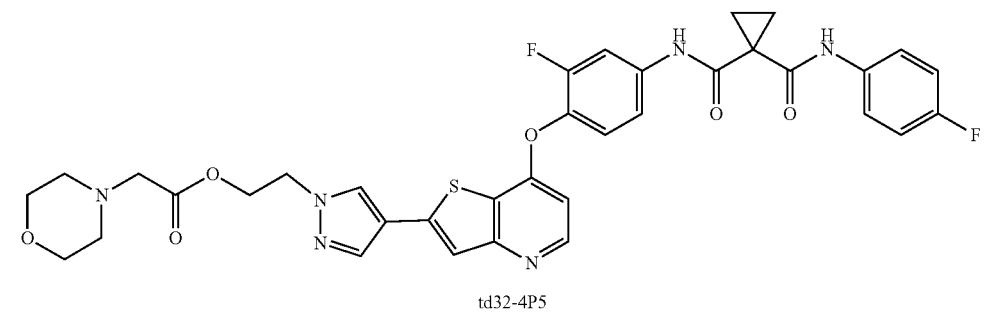

Using 2-morpholino acetic acid (2.523 g, 17.4 mmol) and td32-4 (5 g, 8.7 mmol) as raw materials, referring to the synthetic method of Example 3, 5.02 g of white solid was obtained. Yield: 82.2%, HPLC purity: 96.3%, LC-MS: 703.4 [M+H]$^+$.

Example 6

Synthesis of Compound 2-(4-(7-(2-fluoro-4-(1-((4-fluorophenyl)carbamoyl)cyclopropane-1-carboxamide)phenoxy)thieno[3,2-b]pyridin-2-yl)-1H-pyrazolyl-1-yl)ethyl glycinate (td32-4P6)

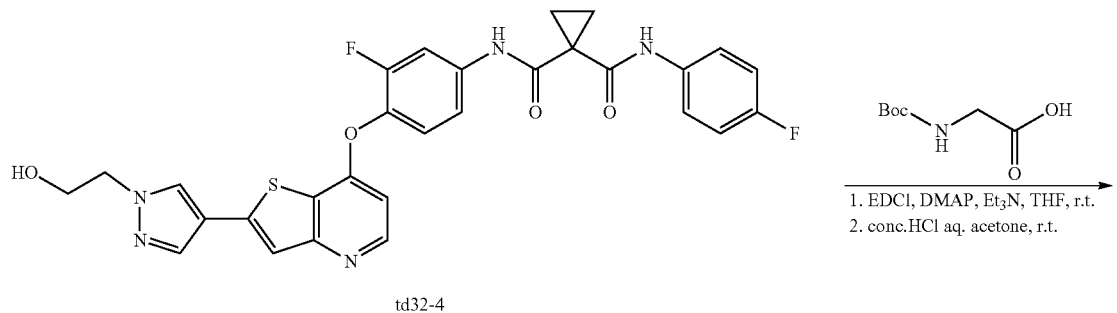

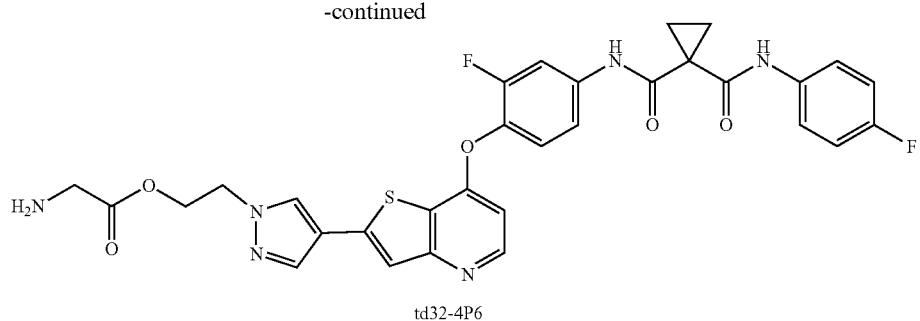

td32-4P6

1) Synthesis of Compound 6A: 2-(4-(7-(2-fluoro-4-(1-((4-fluorophenyl)carbamoyl) cyclopropane-1-carboxamide)phenoxy)thieno[3,2-b]pyridin-2-yl)-1H-pyrazolyl-1-yl)ethyl(tert-butoxycarbonyl) glycinate At 0° C., Boc-glycine (3.04 g, 17.4 mmol), 1-ethyl-(3-dimethylaminopropyl)carbodiimide hydrochloride (EDCI, 4 g, 20.9 mmol), 4-dimethylaminopyridine (DMAP, 1.59 g, 13.0 mmol) were added to 60 mL of anhydrous tetrahydrofuran and reacted for 30 min. td32-4 (5 g, 8.7 mmol) was added to the reaction system, and reacted for 24 hours at room temperature. The reaction solution was filtered, 200 mL of 1 mol/L dilute hydrochloric acid solution was added to the filtrate, stirred to precipitate a white solid, and filtered with suction. The solid was dried to obtain crude intermediate product, which was recrystallized with water/ethanol (V/V=1/1) to obtain Intermediate 6A as 4.81 g of white solid. Yield: 75.5%.

2) Synthesis of Compound td32-4P6

Intermediate 6A was dissolved in 30 mL of anhydrous acetone, 2 mL of concentrated hydrochloric acid was added, and reacted at 40° C. for 5 hours to produce a white precipitate. The mixture was filtered with suction, and the filter cake was washed with 20 mL of anhydrous acetone, and dried under vacuum to obtain hydrochloride salt of td32-4P6 as 3.97 g of white solid. Yield: 95.1%, HPLC purity: 98.5%, LC-MS: 632.3 [M+H]$^+$.

Example 7

2-(4-(7-(2-fluoro-4-(1-((4-fluorophenyl)carbamoyl) cyclopropane-1-carboxamide)phenoxy) thieno[3,2-b]pyridin-2-yl)-1H-pyrazolyl-1-yl)ethyl alaninate (td32-4P7)

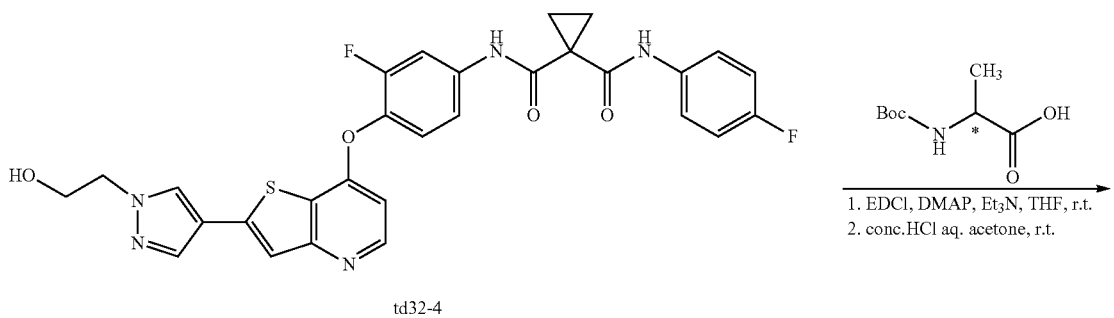

td32-4

1. EDCl, DMAP, Et$_3$N, THF, r.t.
2. conc.HCl aq. acetone, r.t.

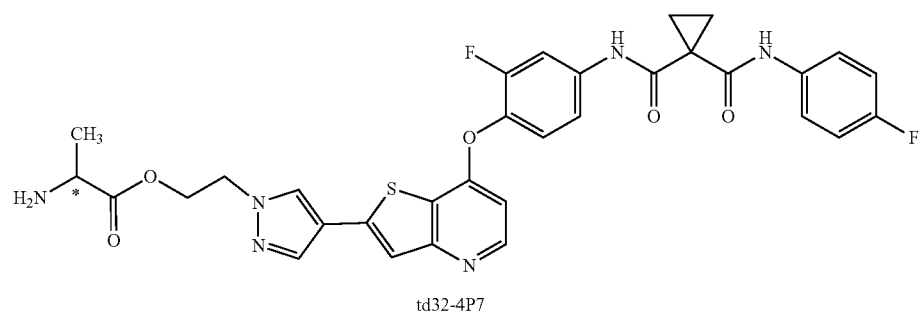

td32-4P7

1) Synthesis of Compound 7A: 2-(4-(7-(2-fluoro-4-(1-((4-fluorophenyl)carbamoyl) cyclopropane-1-carboxamide)phenoxy)thieno[3,2-b]pyridin-2-yl)-1H-pyrazolyl-1-yl)ethyl(tert-butoxycarbonyl) alaninate Using Boc-alanine (3.29 g, 17.4 mmol) and td32-4 (5 g, 8.7 mmol) as raw materials, referring to the synthetic method of 6A in Example 6, Compound 7A was obtained. White solid 5.21 g, yield: 80.2%.

Synthesis of Compound td32-4P7

Using Compound 7A as a raw material referring to the synthetic method of td32-4P6 in Example 6, Compound 2-(4-(7-(2-fluoro-4-(1-((4-fluorophenyl)carbamoyl)cyclopropane-1-carboxamide)phenoxy)thieno[3,2]pyridin-2-yl)-1H-pyrazol-1-yl)ethyl alaninate (td32-4P7) hydrochloride was obtained. White solid 4.29 g, yield: 90.1%, HPLC purity: 98.1%, LC-MS: 647.3 [M+H]$^+$.

Example 8

Synthesis of Compound 2-(4-(7-(2-fluoro-4-(1-((4-fluorophenyl)carbamoyl)cyclopropane-1-carboxamide)phenoxy)thieno[3,2-b]pyridin-2-yl)-1H-pyrazolyl-1-yl)ethyl leucinate (td32-4P8)

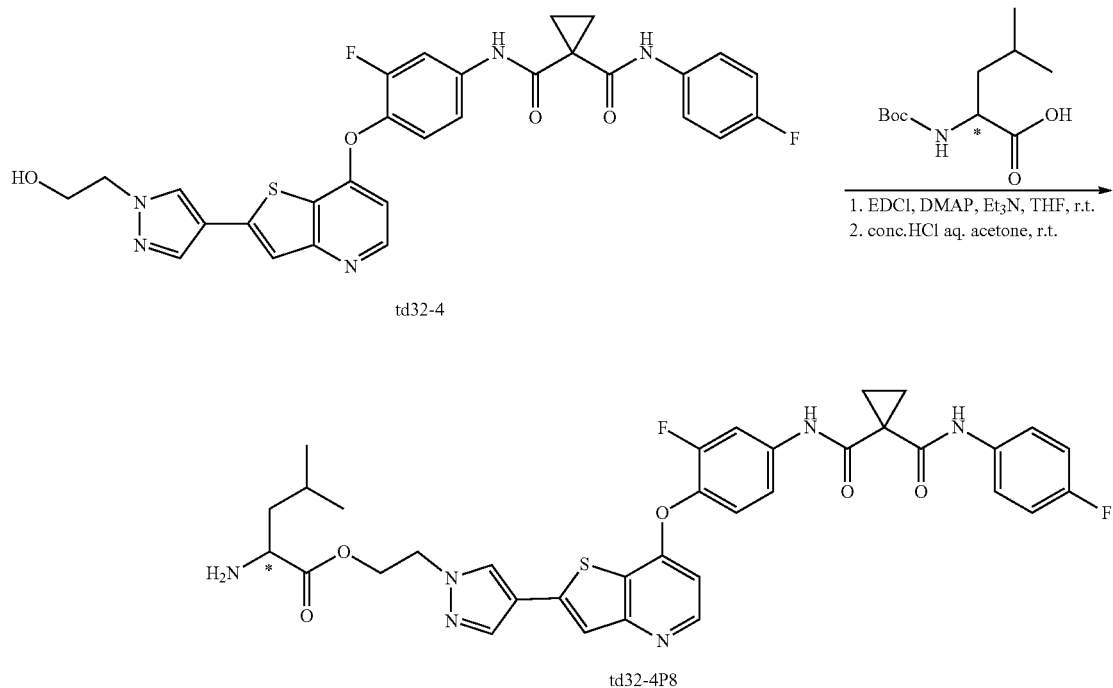

1) Synthesis of Compound 8A: 2-(4-(7-(2-fluoro-4-(1-((4-fluorophenyl)carbamoyl) cyclopropane-1-carboxamide)phenoxy)thieno[3,2-b]pyridin-2-yl)-1H-pyrazolyl-1-yl)ethyl(tert-butoxycarbonyl) leucinate Using Boc-leucine (4.02 g, 17.4 mmol) and td32-4 (5 g, 8.7 mmol) as raw materials, referring to the synthetic method of 6A in Example 6, Compound 8A was obtained. White solid 4.47 g, yield: 65.1%.

2) Synthesis of Compound td32-4P8

Using compound 8A as a raw material, referring to the synthetic method of td32-4P6 in Example 6, Compound 2-(4-(7-(2-fluoro-4-(1-((4-fluorophenyl)carbamoyl))cyclopropane-1-carboxamide)phenoxy)thieno[3,2-b]pyridin-2-yl)-1H-pyrazol-1-yl)ethyl leucinate (td32-4P8) was obtained. White solid 3.66 g, yield: 89.2%, HPLC purity: 99.0%, LC-MS: 689.8 [M+H]$^+$.

Example 9

Synthesis of Compound 2-(4-(7-(2-fluoro-4-(1-(4-fluorophenyl)carbamoyl)cyclopropane-1-carboxamide)phenoxy)thieno[3,2-b]pyridin-2-yl)-1H-pyrazolyl-1-yl)ethyl isoleucinate (td32-4P9)

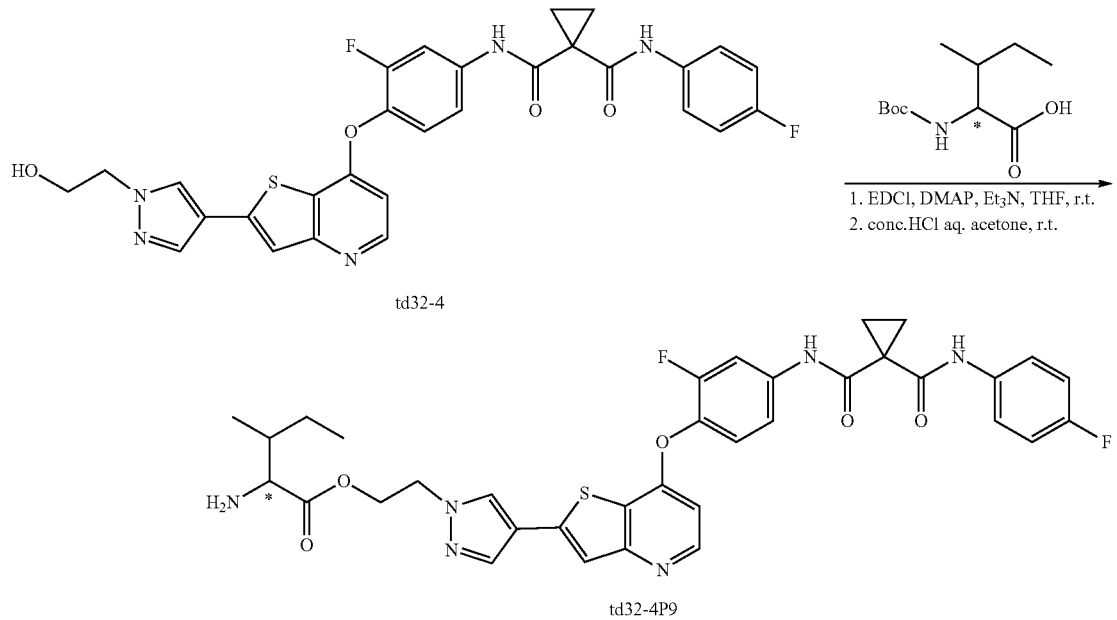

1) Synthesis of Compound 9A: 2-(4-(7-(2-fluoro-4-(1-((4-fluorophenyl)carbamoyl) cyclopropane-1-carboxamide)phenoxy)thieno[3,2-b]pyridin-2-yl)-1H-pyrazolyl-1-yl)ethyl(tert-butoxycarbonyl) isoleucinate Using Boc-isoleucine (4.02 g, 17.4 mmol) and td32-4 (5 g, 8.7 mmol) as raw materials, referring to the synthetic method of 6A in Example 6, Compound 9A was obtained. White solid 4.88 g, yield: 71.2%.

2) Synthesis of Compound td32-4P9

Using Compound 9A as a raw material, referring to the synthetic method of td32-4P6 in Example 6, Compound 2-(4-(7-(2-fluoro-4-(1-((4-fluorophenyl)carbamoyl))cyclopropane-1-carboxamide)phenoxy)thieno[3,2-b]pyridin-2-yl)-1H-pyrazol-1-yl)ethyl isoleucinate (td32-4P9) was obtained. White solid 3.85 g, yield: 85.7%, HPLC purity: 97.3%, LC-MS: 689.7 [M+H]$^+$.

Example 10

Synthesis of Compound 2-(4-(7-(2-fluoro-4-(1-((4-fluorophenyl)carbamoyl)cyclopropane-1-carboxamide)phenoxy)thieno[3,2-b]pyridin-2-yl)-1H-pyrazolyl-1-yl)ethyl valinate (td32-4P10)

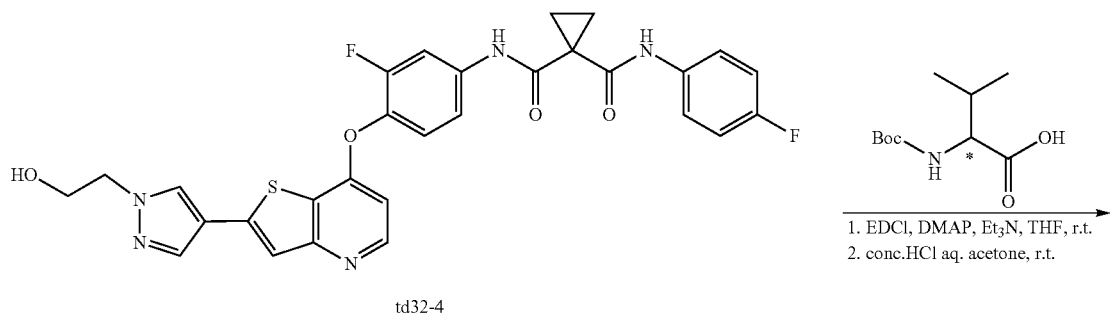

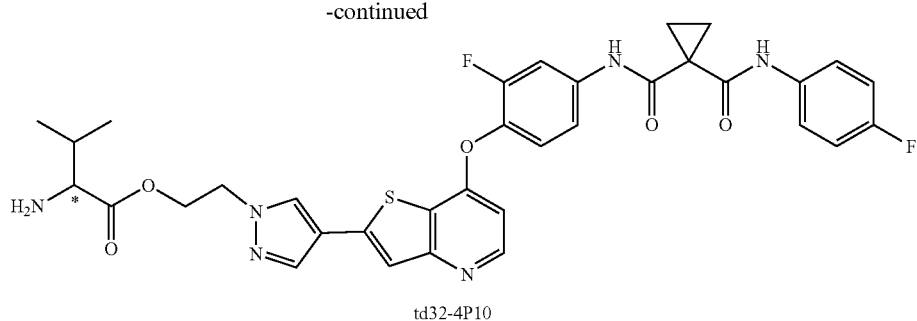

td32-4P10

1) Synthesis of Compound 10A: 2-(4-(7-(2-fluoro-4-(1-((4-fluorophenyl)carbamoyl) cyclopropane-1-carboxamide)phenoxy)thieno[3,2-b]pyridin-2-yl)-1H-pyrazolyl-1-yl)ethyl(tert-butoxycarbonyl) valinate Using Boc-valine (3.77 g, 17.4 mmol) and td32-4 (5 g, 8.7 mmol) as raw materials, with reference to the synthetic method of 6A in Example 6, Compound 10A was obtained. White solid 5.33 g, yield: 79.1%.

2) Synthesis of Compound td32-4P10

Using Compound 10A as a raw material, referring to the synthetic method of td32-4P6 in Example 6, Compound 2-(4-(7-(2-fluoro-4-(1-((4-fluorophenyl)carbamoyl)cyclopropane-1-carboxamide)phenoxy)thieno[3,2-b]pyridin-2-yl)-1H-pyrazol-1-yl)ethyl valinate (td32-4P10) was obtained. White solid 4.46 g, yield: 91.1%, HPLC purity: 97.2%, LC-MS: 675.8 [M+H]⁺.

Example 11

Synthesis of Compound 2-(4-(7-(2-fluoro-4-(1-((4-fluorophenyl)carbamoyl)cyclopropane-1-carboxamide)phenoxy)thieno[3,2-b]pyridin-2-yl)-1H-pyrazolyl-1-yl)ethyl methioninate (td32-4P11)

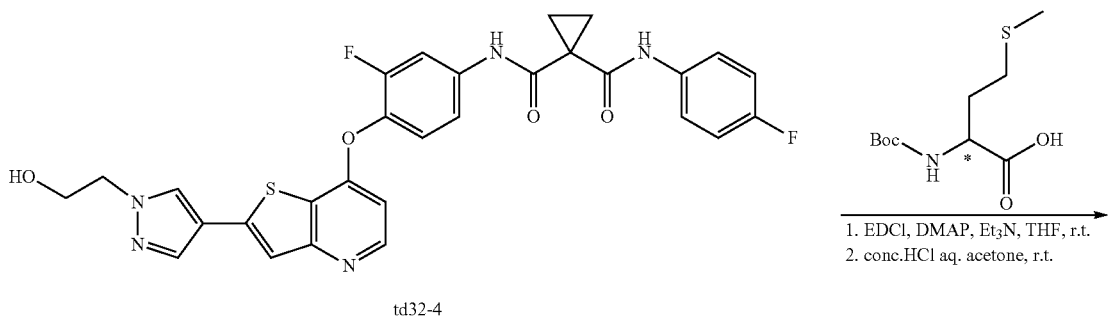

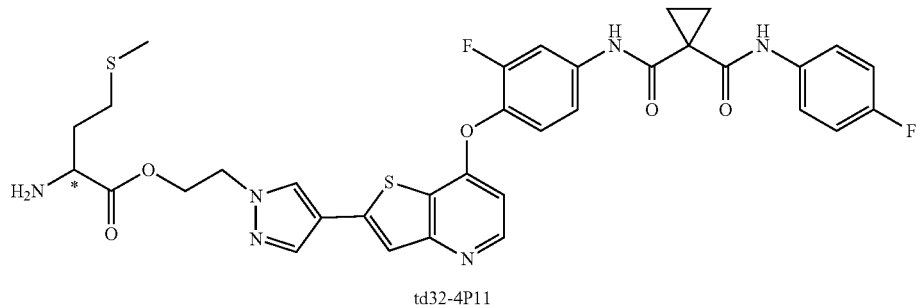

td32-4P11

1) Synthesis of Compound 11A: 2-(4-(7-(2-fluoro-4-(1-((4-fluorophenyl)carbamoyl) cyclopropane-1-carboxamide)phenoxy)thieno[3,2-b]pyridin-2-yl)-1H-pyrazolyl-1-yl)ethyl(tert-butoxycarbonyl) methioninate Using Boc-methionine (4.33 g, 17.4 mmol) and td32-4 (5 g, 8.7 mmol) as raw materials, referring to the synthetic method of 6A in Example 6, Compound 11A was obtained. White solid 4.64 g, yield: 66.1%.

2) Synthesis of Compound td32-4P11

Using Compound 11A as a raw material, referring to the synthetic method of td32-4P6 in Example 6, Compound 2-(4-(7-(2-fluoro-4-(1-(4-fluorophenyl)carbamoyl)cyclopropane carboxamide)phenoxy)thieno[3,2-b]pyridin-2-yl)-1H-pyrazol-1-yl)ethyl L-methioninate (td32-4P11) was obtained. White solid 4.03 g, yield: 94.3%, HPLC purity: 97.3%, LC-MS: 707.9 [M+H]+.

Example 12

Synthesis of Compound 2-(4-(7-(2-fluoro-4-(1-((4-fluorophenyl)carbamoyl)cyclopropane-1-carboxamide)phenoxy)thieno[3,2-b]pyridin-2-yl)-1H-pyrazolyl-1-yl)ethyl L-phenylalaninate (td32-4P12)

1) Synthesis of Compound 12A: 2-(4-(7-(2-fluoro-4-(1-((4-fluorophenyl)carbamoyl) cyclopropane-1-carboxamide)phenoxy)thieno[3,2-b]pyridin-2-yl)-1H-pyrazolyl-1-yl)ethyl(tert-butoxycarbonyl) phenylalaninate Using Boc-phenylalanine (4.61 g, 17.4 mmol) and td32-4 (5 g, 8.7 mmol) as raw materials, referring to the synthetic method of 6A in Example 6, Compound 12A was obtained. White solid 5.07 g, yield: 70.8%.

2) Synthesis of Compound td32-4P12

Using Compound 12A as a raw material, referring to the synthetic method of td32-4P6 in Example 6, Compound 2-(4-(7-(2-fluoro-4-(1-((4-fluorophenyl)carbamoyl))cyclopropane-1-carboxamide)phenoxy)thieno[3,2-b]pyridin-2-yl)-1H-pyrazol-1-yl)ethyl L-phenylalaninate (td32-4P12) hydrochloride was obtained. White solid 4.38 g, yield: 93.6%, HPLC purity: 98.1%, LC-MS: 723.8 [M+H]+.

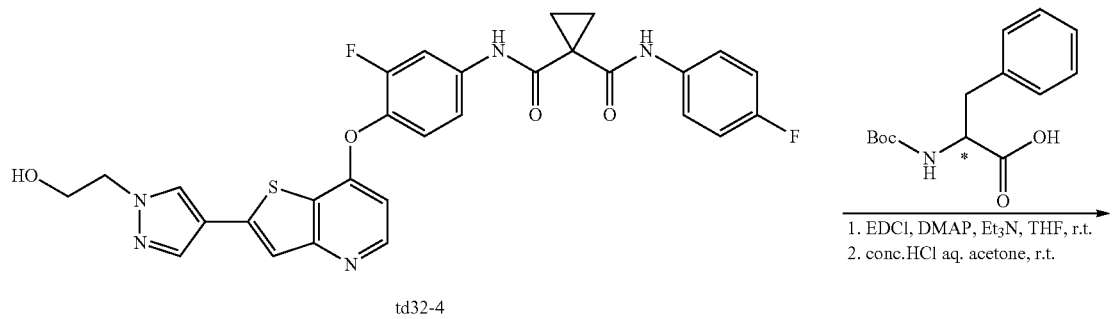

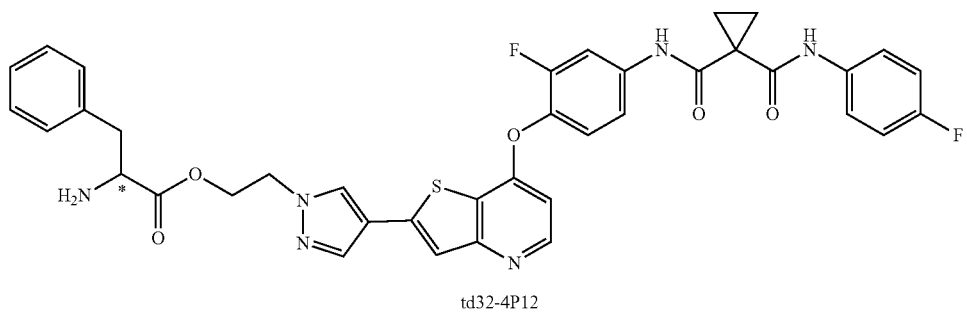

td32-4P12

Example 13

Synthesis of Compound 2-(4-(7-(2-fluoro-4-(1-((4-fluorophenyl)carbamoyl)cyclopropane-1-carboxamide)phenoxy)thieno[3,2-b]pyridin-2-yl)-1H-pyrazolyl-1-yl)ethyl prolinate (td32-4P13)

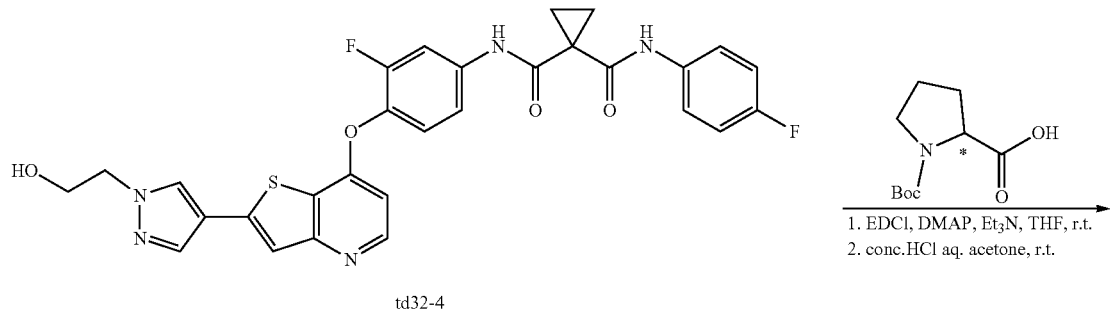

1) Synthesis of Compound 13A: 2-(4-(7-(2-fluoro-4-(1-((4-fluorophenyl)carbamoyl) cyclopropane-1-carboxamide)phenoxy)thieno[3,2-b]pyridin-2-yl)-1H-pyrazolyl-1-yl)ethyl(tert-butoxycarbonyl)prolinate Using Boc-proline (3.74 g, 17.4 mmol) and td32-4 (5 g, 8.7 mmol) as raw materials, referring to the synthetic method of 6A in Example 6, Compound 13A was obtained. White solid 6.72 g, yield: 77.4%.

2) Synthesis of Compound td32-4P13

Using Compound 13A as a raw material, referring to the synthetic method of td32-4P6 in Example 6, Compound 2-(4-(7-(2-fluoro-4-(1-((4-fluorophenyl)carbamoyl)cyclopropane carboxamide)phenoxy)thieno[3,2-b]pyridin-2-yl)-1H-pyrazolyl-1-yl)ethyl L-prolinate (td32-4P13) hydrochloride was obtained. White solid 4.27 g, yield: 89.4%, HPLC purity: 95.1%, LC-MS: 673.6 [M+H]$^+$.

Example 14

Synthesis of Compound 2-(4-(7-(2-fluoro-4-(1-((4-fluorophenyl)carbamoyl)cyclopropane-1-carboxamide)phenoxy)thieno[3,2-b]pyridin-2-yl)-1H-pyrazolyl-1-yl)ethyl asparaginate (td32-4P15)

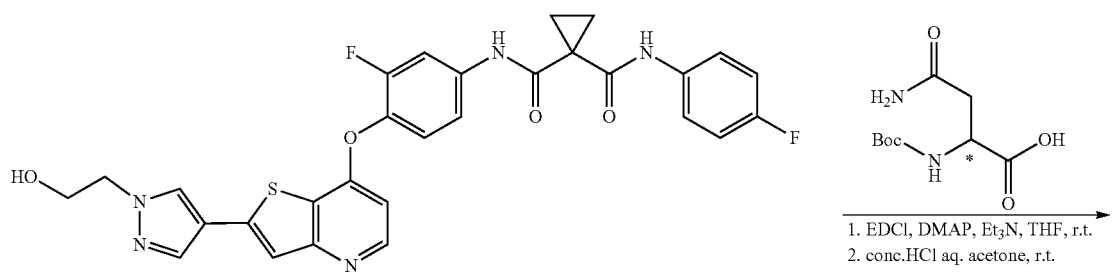

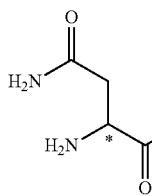
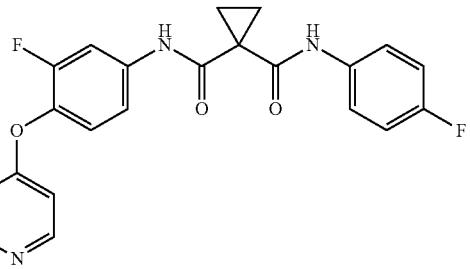

td32-4P14

1) Synthesis of Compound 14A: 2-(4-(7-(2-fluoro-4-(1-((4-fluorophenyl)carbamoyl) cyclopropane-1-carboxamide)phenoxy)thieno[3,2-b]pyridin-2-yl)-1H-pyrazolyl-1-yl)ethyl(tert-butoxycarbonyl) asparagine ester Using Boc-asparagine (4.03 g, 17.4 mmol) and td32-4 (5 g, 8.7 mmol) as raw materials, referring to the synthetic method of 6A in Example 6, Compound 14A was obtained. White solid 4.05 g, yield: 58.9%.

2) Synthesis of Compound td32-4P14

Using compound 14A as a raw material, referring to the synthetic method of td32-4P6 in Example 6, Compound 2-(4-(7-(2-fluoro-4-(1-((4-fluorophenyl)carbamoyl))cyclopropane-1-carboxamide)phenoxy)thieno[3,2-b]pyridin-2-yl)-1H-pyrazol-1-yl)ethyl asparagine ester (td32-4P14) hydrochloride was obtained. White solid 3.17 g, yield: 85.3%, HPLC purity: 97.9%, LC-MS: 691.1 [M+H]+.

Example 15

Synthesis of Compound 2-(4-(7-(2-fluoro-4-(1-((4-fluorophenyl)carbamoyl)cyclopropane-1-carboxamide)phenoxy)thieno[3,2-b]pyridin-2-yl)-1H-pyrazolyl-1-yl)ethyl glutaminate (td32-4P15)

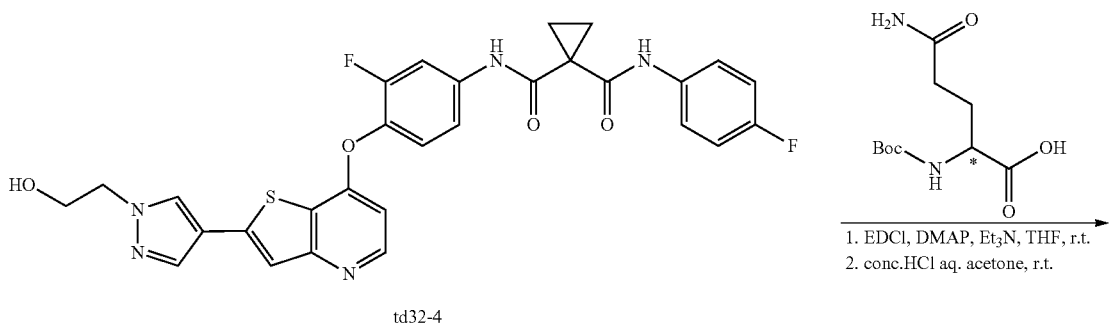

td32-4

1. EDCl, DMAP, Et₃N, THF, r.t.
2. conc.HCl aq. acetone, r.t.

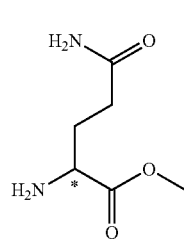
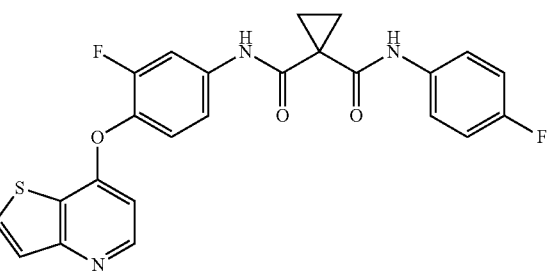

td32-4P15

1) Synthesis of Compound 15A: 2-(4-(7-(2-fluoro-4-(1-((4-fluorophenyl)carbamoyl) cyclopropane-1-carboxamide)phenoxy)thieno[3,2-b]pyridin-2-yl)-1H-pyrazolyl-1-yl)ethyl(tert-butoxycarbonyl) glutamine ester Using Boc-glutamine (4.28 g, 17.4 mmol) and td32-4 (5 g, 8.7 mmol) as raw materials, referring to the synthetic method of 6A in Example 6, Compound 15A was obtained. White solid 3.90 g, yield: 55.8%.

2) Synthesis of Compound td32-4P15

Using Compound 15A as a raw material, referring to the synthetic method of td32-4P6 in Example 6, Compound 2-(4-(7-(2-fluoro-4-(1-((4-fluorophenyl)carbamoyl)cyclopropane-1-carboxamide)phenoxy)thieno[3,2-b]pyridin-2-yl)-1H-pyrazolyl-1-yl)ethyl L-glutamine ester (td32-4P15) hydrochloride was obtained. White solid 2.99 g, yield: 83.3%, HPLC purity: 99.0%, LC-MS: 704.6 [M+H]$^+$.

Example 16

Synthesis of Compound 2-(4-(7-(2-fluoro-4-(1-(4-fluorophenyl)carbamoyl)cyclopropane-1-carboxamide)phenoxy)thieno[3,2-b]pyridin-2-yl)-1H-pyrazolyl-1-yl)ethyl tryptophanate (td32-4P16)

1) Synthesis of Compound 16A: 2-(4-(7-(2-fluoro-4-(1-((4-fluorophenyl)carbamoyl) cyclo propane-1-carboxamide)phenoxy)thieno[3,2-b]pyridin-2-yl)-1H-pyrazolyl-1-yl)ethyl(tert-butoxycarbonyl) tryptophanate Using Boc-tryptophan (5.29 g, 17.4 mmol) and td32-4 (5 g, 8.7 mmol) as raw materials, referring to the synthetic method of 6A in Example 6, Compound 16A was obtained. White solid 4.89 g, yield: 65.3%.

2) Synthesis of Compound td32-4P16

Using Compound 16A as a raw material, referring to the synthetic method of td32-4P7 in Example 7, Compound 2-(4-(7-(2-fluoro-4-(1-((4-fluorophenyl)carbamoyl))cyclopropane carboxamide)phenoxy)thieno[3,2-b]pyridin-2-yl)-1H-pyrazolyl-1-yl)ethyl L-tryptophanate (td32-4P16) hydrochloride was obtained. White solid 3.48 g, yield: 76.7%, HPLC purity: 94.6%, LC-MS: 762.7 [M+H]

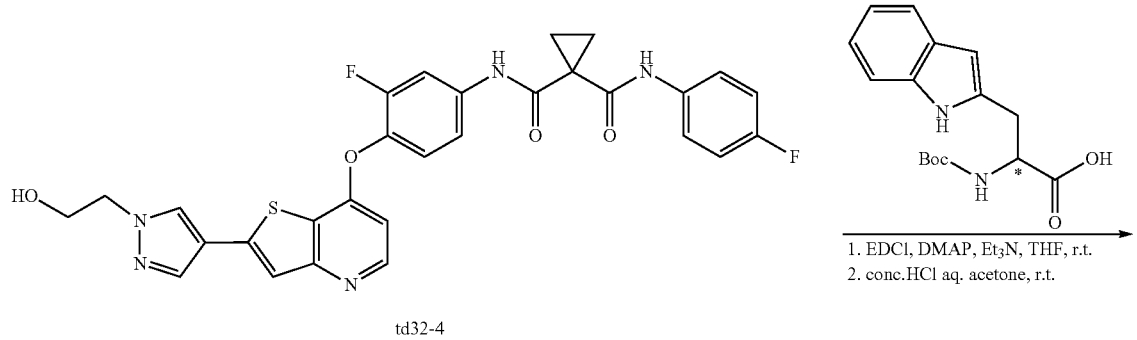

td32-4

1. EDCl, DMAP, Et$_3$N, THF, r.t.
2. conc.HCl aq. acetone, r.t.

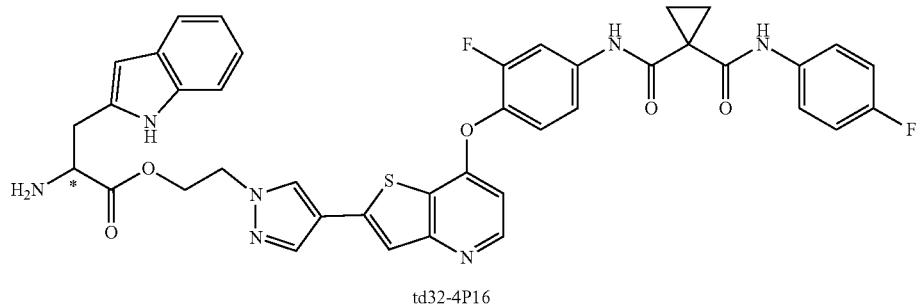

td32-4P16

Example 17

2-(4-(7-(2-fluoro-4-(1-((4-fluorophenyl)carbamoyl) cyclopropane-1-carboxamide)phenoxy) thieno[3,2-b]pyridin-2-yl)-1H-pyrazolyl-1-yl)ethyl(2,2-dimethoxyethyl) glycinate (td32-4P17)

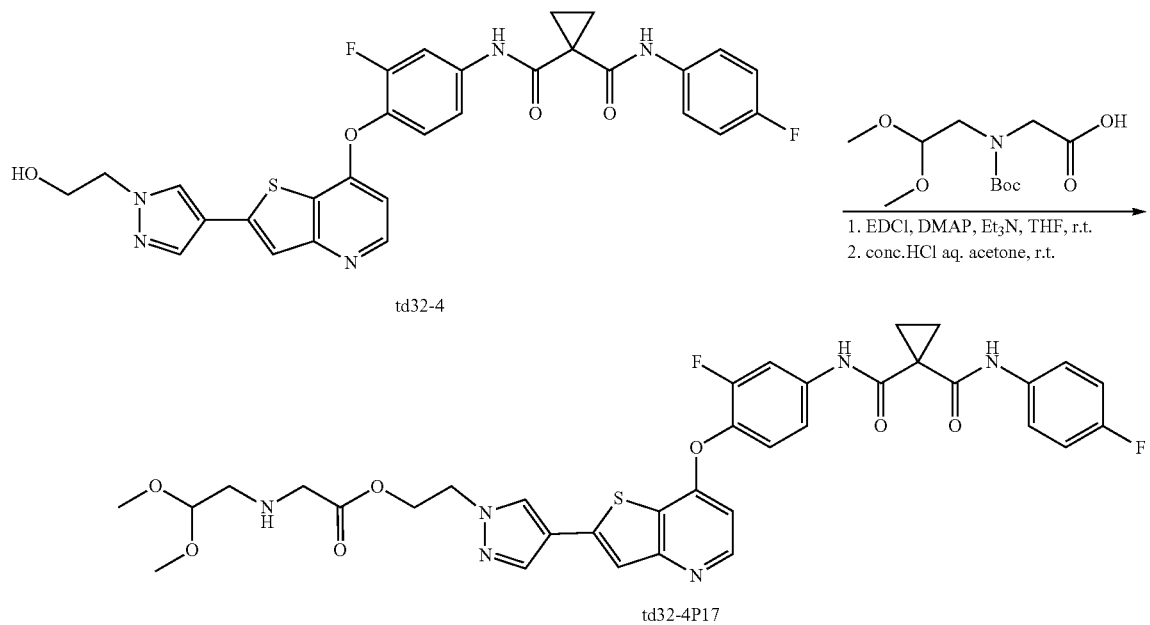

1) Synthesis of Compound 17A: 2-(4-(7-(2-fluoro-4-(1-((4-fluorophenyl)carbamoyl)cyclo propane-1-carboxamide)phenoxy)thieno[3,2-b]pyridin-2-yl)-1H-pyrazolyl-1-yl)ethyl(2,2-dimeth oxyethyl)(tert-butoxycarbonyl) glycinate Using N-Boc-N-2,2-dimethoxyethylglycine (4.57 g, 17.4 mmol) and td32-4 (5 g, 8.7 mmol) as raw materials, referring to the synthetic method of 6A in Example 6, Compound 17A was obtained. White solid 5.50 g, yield: 77.1%.

2) Synthesis of Compound td32-4P17

Using Compound 17A as a raw material, referring to the synthetic method of td32-4P6 in Example 6, Compound 2-(4-(7-(2-fluoro-4-(1-((4-fluorophenyl)carbamoyl)cyclopropane-1-carboxamide)phenoxy)thieno[3,2-b]pyridin-2-yl)-1H-pyrazolyl-1-yl)ethyl(2,2-dimethoxyethyl) glycinate (td32-4P17) hydrochloride. White solid 4.53 g, yield: 89.3%, HPLC purity: 93.5%, LC-MS: 721.9 [M+H]$^+$.

Example 18

Synthesis of Compound 2-(4-(7-(2-fluoro-4-(1-((4-fluorophenyl)carbamoyl)cyclopropane-1-carboxamide)phenoxy)thieno[3,2-b]pyridin-2-yl)-1H-pyrazolyl-1-yl)ethyl N,N-dimethyl alaninate (td32-4P18)

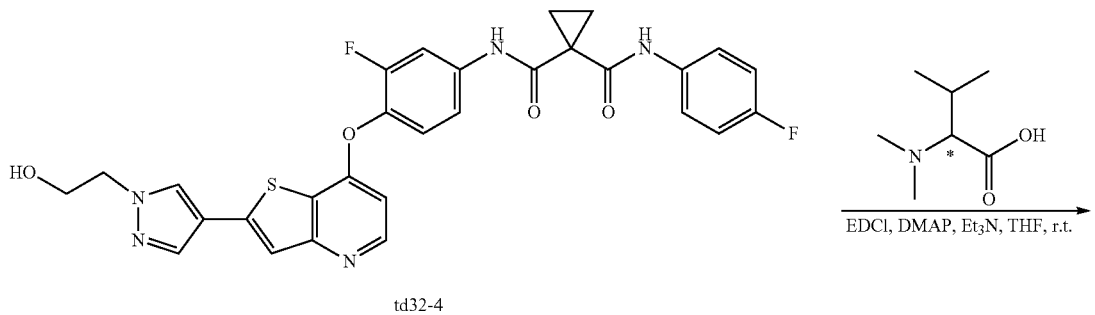

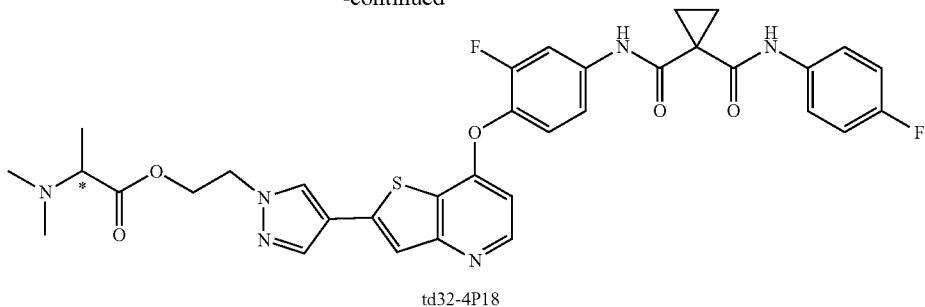

td32-4P18

Using N,N-dimethylalanine (2.03 g, 17.4 mmol) and td32-4 (5 g, 8.7 mmol) as raw materials, referring to the synthetic method of Example 3, 5.86 g of white solid was obtained, yield: 76.1%, HPLC purity: 93.3%, LC-MS: 675.3 [M+H]$^+$.

Example 19

Synthesis of Compound 2-(4-(7-(2-fluoro-4-(1-((4-fluorophenyl)carbamoyl)cyclopropane-1-carboxamide)phenoxy)thieno[3,2-b]pyridin-2-yl)-1H-pyrazolyl-1-yl)ethyl 4-(morpholinylmethyl) benzoate (td32-4P19)

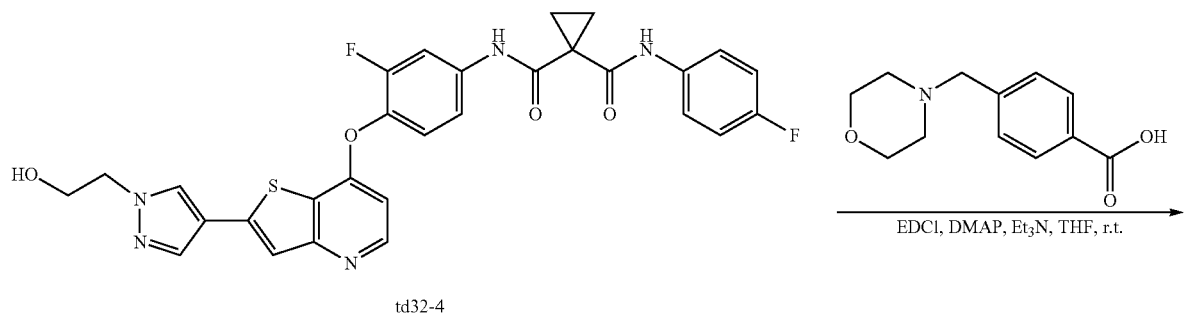

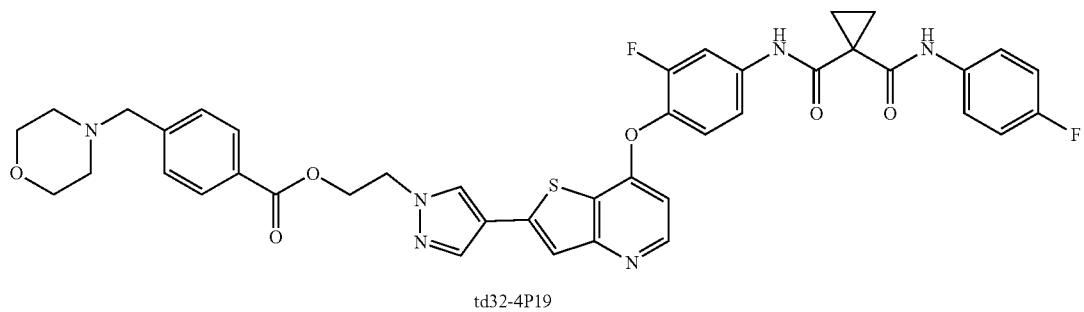

td32-4P19

Using 4-(morpholinomethyl)benzoic acid (3.84 g, 17.4 mmol) and td32-4 (5 g, 8.7 mmol) as raw materials, referring to the synthetic method of Example 3, 4.50 g of white solid was obtained, yield: 66.5%, HPLC purity: 95.9%, LC-MS: 780.1 [M+H]$^+$.

Example 20

Synthesis of Compound 2-(4-(7-(2-fluoro-4-(1-((4-fluorophenyl)carbamoyl)cyclopropane-1-carboxamide)phenoxy)thieno[3,2-b]pyridin-2-yl)-1H-pyrazolyl-1-yl)ethyl 3-(morpholinylmethyl) benzoate (td32-4P20)

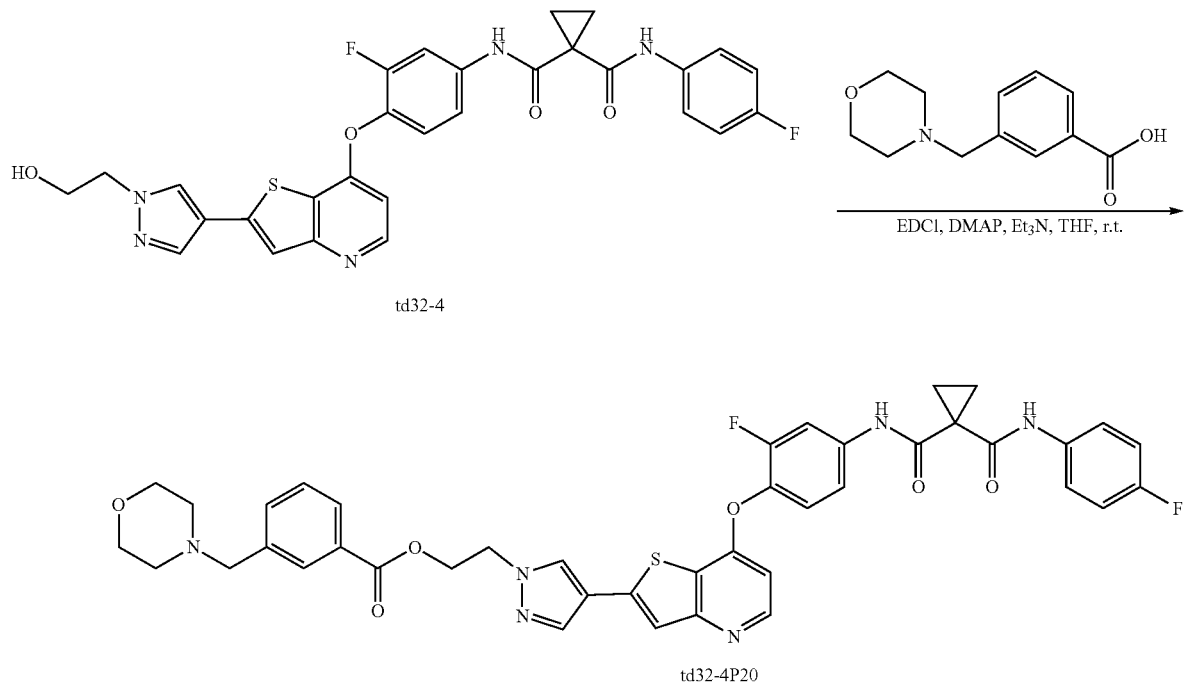

Using 3-(morpholinylmethyl)benzoic acid (3.84 g, 17.4 mmol) and td32-4 (5 g, 8.7 mmol) as raw materials, referring to the synthetic method of Example 3, 4.68 g of white solid was obtained, yield: 69.1%, HPLC purity: 95.2%, LC-MS: 779.9 [M+H]$^+$.

Example 21

Synthesis of Compound 2-(4-(7-(2-fluoro-4-(1-((4-fluorophenyl)carbamoyl)cyclopropane-1-carboxamide)phenoxy)thieno[3,2-b]pyridin-2-yl)-1H-pyrazol-1-yl)ethyl 4-((methylpiperazin-1-yl) methyl) benzoate (td32-4P21)

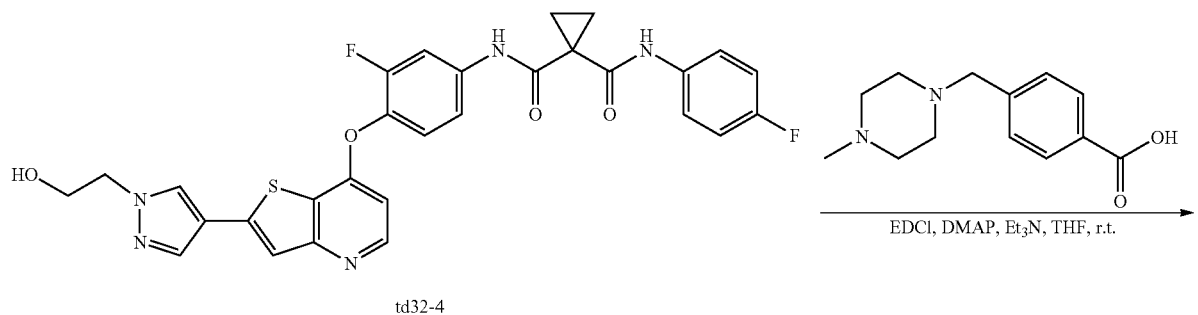

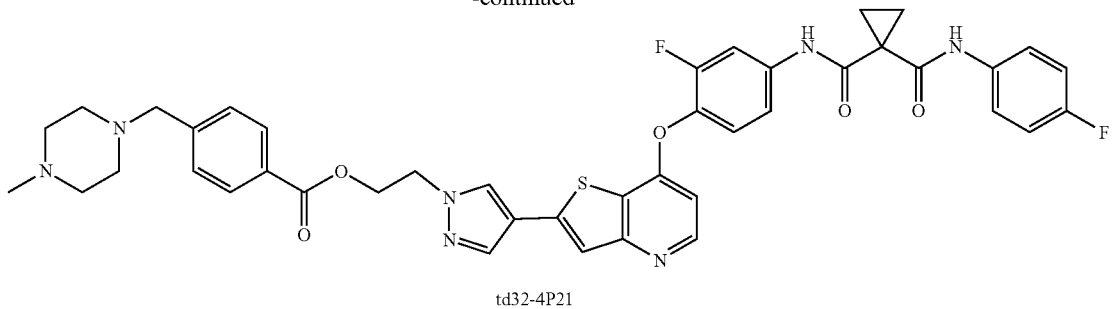

td32-4P21

Using 4-((methylpiperazin-1-yl)methyl)benzoic acid (4.07 g, 17.4 mmol), td32-4 (5 g, 8.7 mmol) as raw materials, referring to the synthetic method of Example 3, 4.14 g of white solid was obtained, yield: 60.1%, HPLC purity: 96.4%, LC-MS: 793.0 [M+H]+.

Example 22

Synthesis of Compound 2-(4-(7-(2-fluoro-4-(1-((4-fluorophenyl)carbamoyl)cyclopropane-1-carboxamide)phenoxy)thieno[3,2-b]pyridin-2-yl)-1H-pyrazolyl-1-yl)ethyl 3-((methylpiperazin-1-yl)methyl)benzoate (td32-4P22)

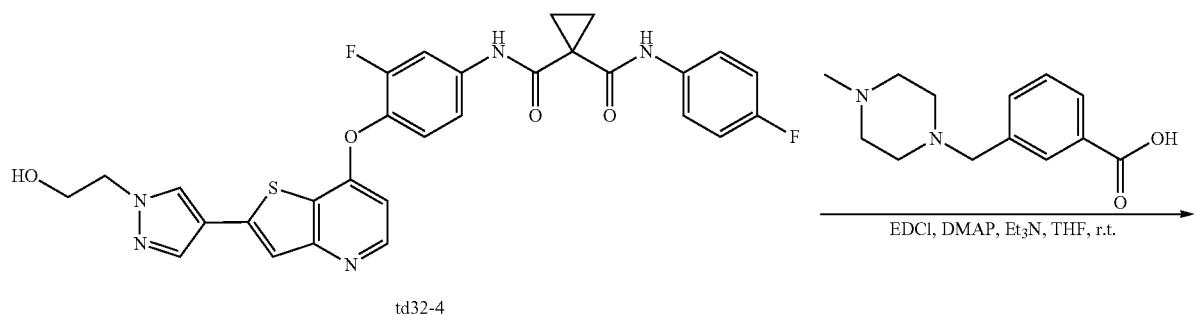

td32-4P22

Using 3-((methylpiperazin-1-yl)methyl)benzoic acid (4.07 g, 17.4 mmol) and td32-4 (5 g, 8.7 mmol) as raw materials, referring to the synthetic method of Example 3, 3.91 g of white solid was obtained, yield: 56.8%, HPLC purity: 93.9%, LC-MS: 792.9 [M+H]+.

Example 23

Synthesis of Compound 2-(4-(7-(2-fluoro-4-(1-((4-fluorophenyl)carbamoyl)cyclopropane-1-carboxamide)phenoxy)thieno[3,2-b]pyridin-2-yl)-1H-pyrazolyl-1-yl)ethyl 4-(pyrrol-1-ylmethyl) benzoate (td32-4P23)

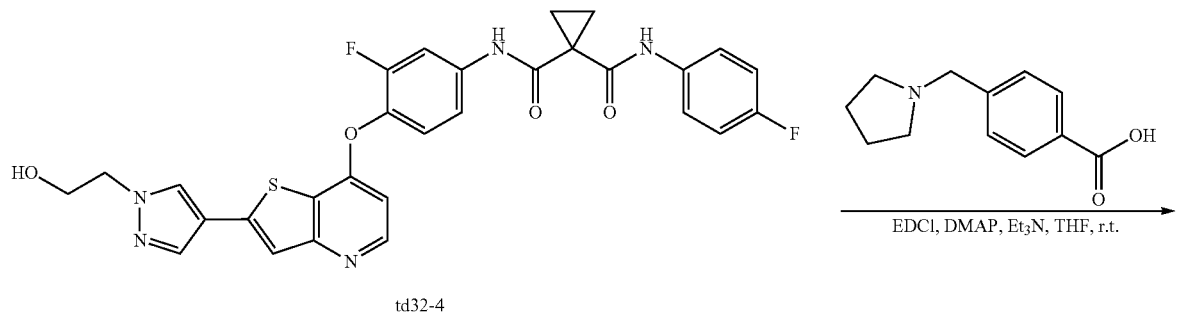

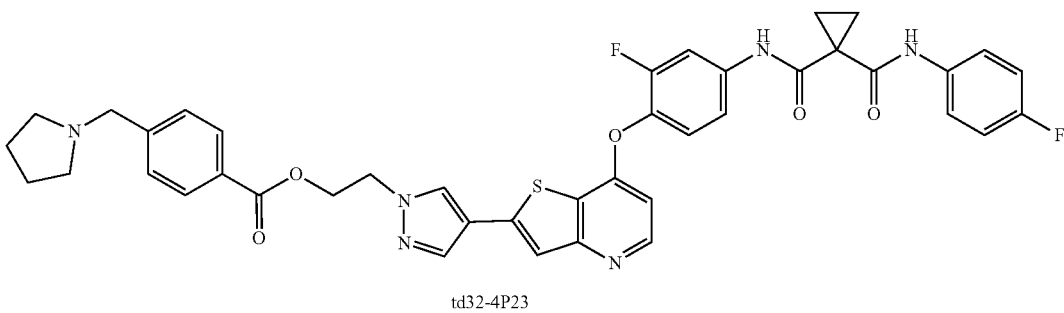

Using 4-(pyrrol-1-ylmethyl) benzoic acid (3.57 g, 17.4 mmol) and td32-4 (5 g, 8.7 mmol) as raw materials, referring to the synthetic method of Example 3, 3.67 g of white solid was obtained, yield: 55.4%, HPLC purity: 96.6%, LC-MS: 763.9 [M+H]$^+$.

Example 24

Synthesis of Compound 2-(4-(7-(2-Fluoro-4-(1-((4-fluorophenyl)carbamoyl)cyclopropane-1-carboxamide)phenoxy)thieno[3,2-b]pyridin-2-yl)-1H-pyrazolyl-1-yl)ethyl 3-(pyrrol-1-yl-methyl) benzoate (td32-4P24)

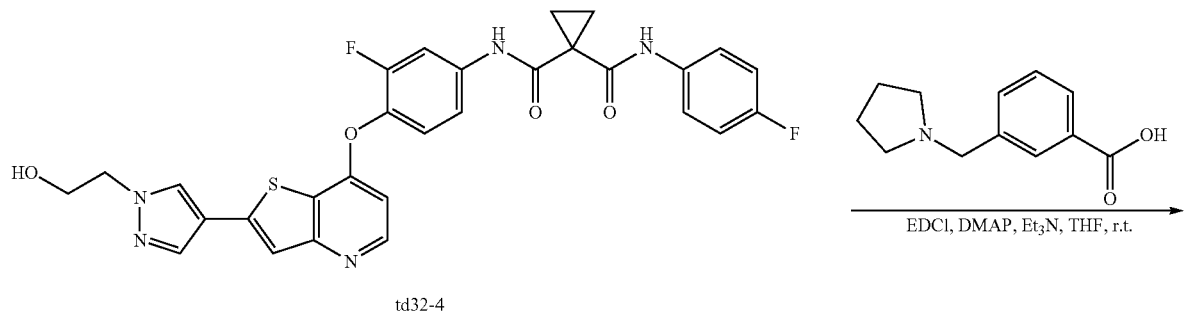

-continued

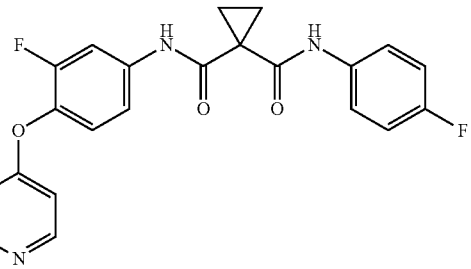

td32-4P22

Using 3-(pyrrol-1-ylmethyl) benzoic acid (3.57 g, 17.4 mmol), td32-4 (5 g, 8.7 mmol) as raw materials, referring to the synthetic method of Example 3, 3.04 g of white solid was obtained, yield:

45.8%, HPLC purity: 97.5%, LC-MS: 763.8 [M+H]$^+$.

Example 25 Solubility Test

The series of compounds synthesized in Examples 1-24 were subjected to solubility test (water), according to the solubility test methods in Chinese Pharmacopoeia, 2015 Edition. The specific test operations and evaluation criteria are as follows:

An appropriate amount (1 mg-10 mg) of finely powdered compound was weighed, placed in a certain volume of solvent at 25° C.±2° C., and shaken vigorously for 30 seconds every 5 minutes; the dissolution within 30 minutes was observed. It was considered completely dissolved if there were no visible particles or droplets of the solute.

| | | |
|---|---|---|
| A | very soluble | 1 g of solute is soluble in less than 1 mL of sovent |
| B | freely soluble | 1 g of solute is soluble in 1~10 mL of sovent |
| C | soluble | 1 g of solute is soluble in 10~30 mL of sovent |
| D | sparingly soluble | 1 g of solute is soluble in 30~100 mL of sovent |
| E | slightly soluble | 1 g of solute is soluble in 100~1000 mL of sovent |
| F | very slightly soluble | 1 g of solute is soluble in 1000~10000 mL of sovent |
| G | practically insoluble or insoluble | 1 g of solute is insoluble in 10000 mL of solvent |

The results of water solubility test of the compounds are shown in Table 1:

TABLE 1

Water solubility test of the compounds

| Compd. | Result |
|---|---|
| td32-4P1 | F |
| td32-4P2 | F |
| td32-4P3 | C |
| td32-4P4 | C |
| td32-4P5 | C |
| td32-4P6 | C |
| td32-4P7 | D |
| td32-4P8 | E |
| td32-4P9 | D |
| td32-4P10 | C |
| td32-4P11 | E |
| td32-4P12 | F |
| td32-4P13 | E |
| td32-4P14 | D |

TABLE 1-continued

Water solubility test of the compounds

| Compd. | Result |
|---|---|
| td32-4P15 | D |
| td32-4P16 | F |
| td32-4P17 | E |
| td32-4P18 | D |
| td32-4P19 | F |
| td32-4P20 | F |
| td32-4P21 | D |
| td32-4P22 | D |
| td32-4P23 | D |
| td32-4P24 | D |
| td32-4 | G |

The experimental results show that the compounds according to the present invention have obviously better water solubility than td32-4, can solve the problem of poor oral absorption caused by low solubility of td32-4, and are expected to be developed as a novel multi-target tyrosine kinase inhibitor drug for treating tumors.

Example 26 In Vivo Transformation Experiment

The compounds of the present invention have improved solubility by introducing a hydrophilic functional group into the structure of td32-4 through an ester bond. After oral administration, the compounds need to be converted into td32-4 in the physical and chemical environment in vivo to exert pharmacological effects. In this example, some representative compounds were selected for in vivo pharmacokinetic studies in SD rats, and compared with direct oral administration of td32-4. The experiment was performed at high (200 mg·kg$^{-1}$) and low (10 mg·kg$^{-1}$) doses.

Experimental Materials:

SD male rats, SPF grade. SIPPR-BK Laboratory Animal Co, Ltd (Shanghai). Other reagents are commercially available products.

1) Preparation of Solution:

Vehicles for Intravenous Administration: DMA+PEG400+ Saline 5 mg of the test sample was placed into a glass bottle. 1 mL of DMA (dimethylacetamide) was added and vortexed to dissolve the solid completely. 1.5 mL of PEG400 was added, vortexed and mixed well. 2.5 mL of physiological saline for injection was added, vortexed, mixed well. The mixture was filtered with a filter membrane (PALL, Nylon, 0.45 μm) to obtain a colorless and clear solution. The test sample was administered to experimental animals (n=3) by tail vein injection at a dose of 5 mg·kg$^{-1}$ (1 mg·mL$^{-1}$).

Vehicle for Oral Administration: PEG400

An appropriate amount of the test sample was placed into a glass bottle. PEG400 was added, vortexed and mixed well. The mixture was sonicated to obtain a clear solution. The test sample was administered to experimental animals (n=3) by gavage at a dose of 10 mg·kg$^{-1}$ and 200 mg·kg$^{-1}$, respectively.

2) Test Method:

SD rats were weighed before administration, and the dose was calculated according to the body weight. They were administered by intravenous injection or by gavage. Blood was collected through the submandibular vein or other suitable ways, at intervals of 0, 0.083, 0.25, 0.5, 1, 2, 4, 8, 12, 24 hours. About 0.20 mL of each sample was collected, anticoagulated with EDTA-K2, and placed on ice after collection, and centrifuged within 1 hour to separate plasma (centrifugation conditions: 6800 g, 6 minutes, 2-8° C.). Plasma samples were stored in a −80° C. freezer prior to analysis. The blood drug concentration of each sample was analyzed using LC-MS/MS. The data of blood drug concentration at different time points were used to calculate pharmacokinetic parameters by Phoenix WinNonlin 7.0, to provide the parameters such as 0-t, AUC0-∞, MRT0-∞, Cmax, Tmax, and T½, and their means and standard deviations. The compounds according to the present invention were all converted into td32-4 after 4 hours of intravenous administration, and the data were regarded as 100% bioavailability, and used to calculate the oral availability.

3) the Representative Experimental Results are as Follows:

Compound Td32-4:

The data of blood drug concentration at 10 mg·kg$^{-1}$ and 200 mg·kg$^{-1}$ are as follows. Through calculation, it can be concluded that the oral bioavailability of Compound td32-4 reached 83.96% at a low concentration, but dropped sharply at a high concentration, only 18.6%. This may be due to the accumulation and precipitation of the compound in the gastrointestinal tract at high concentrations, resulting in inability to be absorbed into the blood circulation. The results are shown in FIG. 1.

Figure 2:
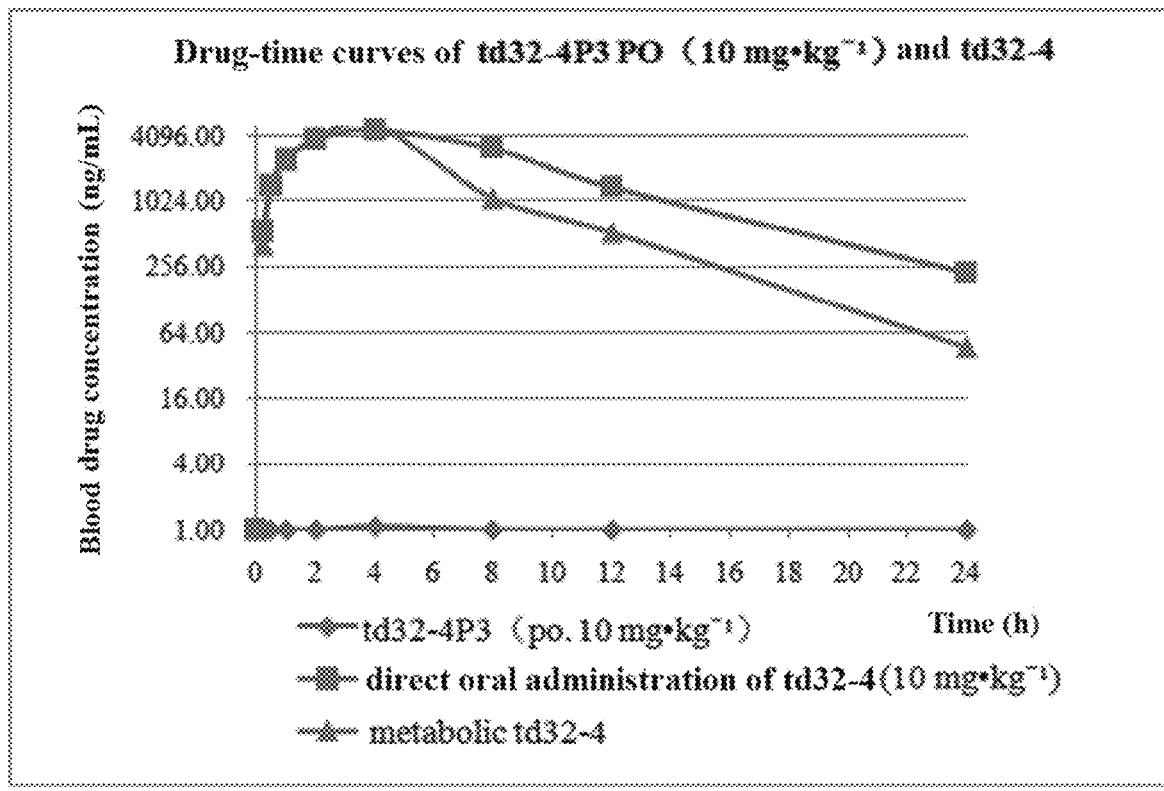
FIG. 2 Blood drug concentration-time curves of td32-4P3, the converted td32-4 in vivo, and td32-4 after oral administration at a dose of 10 mg·kg$^{-1}$.

Compound Td32-4P3 at a Low Concentration:

As shown in FIG. 2, when td32-4P3 was orally administered at a dose of 10 mg·kg$^{-1}$, it could be converted into td32-4 in vivo, and the exposure of td32-4 converted from td32-4P3 in vivo (area under the drug-time curve AUC) was close to that of direct orally administered td32-4, indicating that td32-4P3 was rapidly converted into td32-4 in vivo. The oral bioavailability was calculated as F=70.2% according to the exposure of td32-4.

Figure 3:
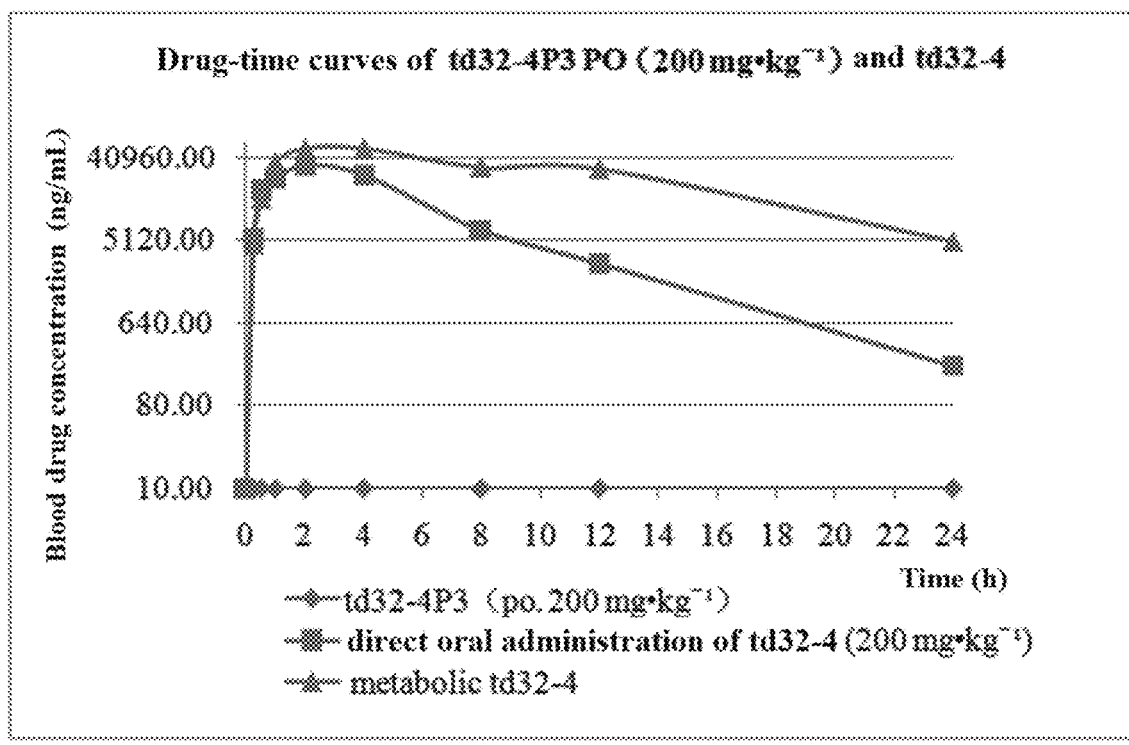
FIG. 3 Blood drug concentration-time curves of td32-4P3, the converted td32-4 in vivo, and td32-4 after oral administration at a dose of 200 mg·kg$^{-1}$.

Compound Td32-4P3 at a High Concentration:

As shown in FIG. 3, when Compound td32-4P3 was orally administered at a dose of 200 mg·kg$^{-1}$, it could be converted into td32-4 in vivo, and the exposure of the converted td32-4 (area under the drug-time curve AUC) was higher than that of direct orally administered td32-4 at a high dose. Td32-4P3 was almost completely converted into td32-4 in vivo within 18 hours, and the oral bioavailability was calculated as F=60.1% according to the exposure of td32-4, which was much higher than that (F=18.6%) of direct orally administered td32-4.

Figure 4:
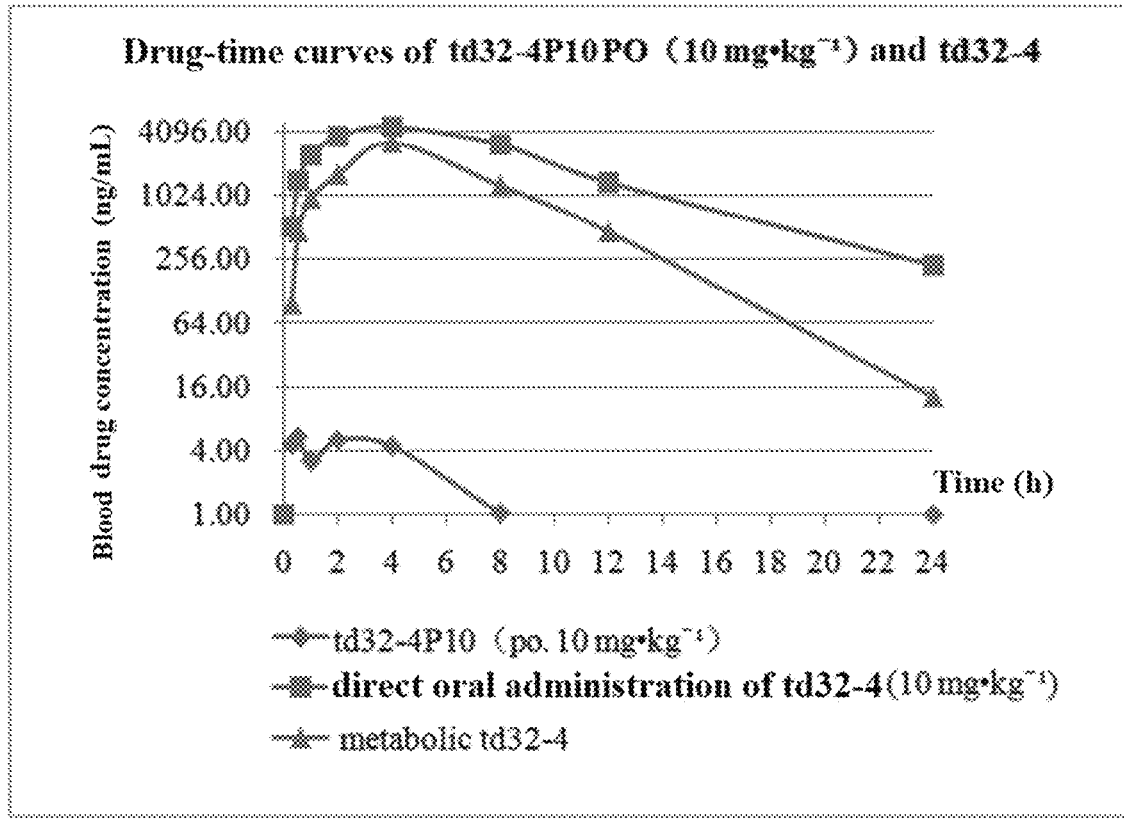
FIG. 4 Blood drug concentration-time curves of td32-4P10, the converted td32-4 in vivo, and td32-4 after oral administration at a dose of 10 mg·kg$^{-1}$.

Compound Td32-4P10 at a Low Concentration:

As shown in FIG. 4, when td32-4P10 was orally administered at a dose of 10 mg·kg$^{-1}$, it could be converted into td32-4 in vivo, and the exposure of the converted td32-4 (area under the drug-time curve AUC) was close to that of direct orally administered td32-4. Td32-4P3 was rapidly converted to td32-4 in vivo. The oral bioavailability was calculated as F=48.9% according to the exposure of the converted td32-4.

Figure 5:
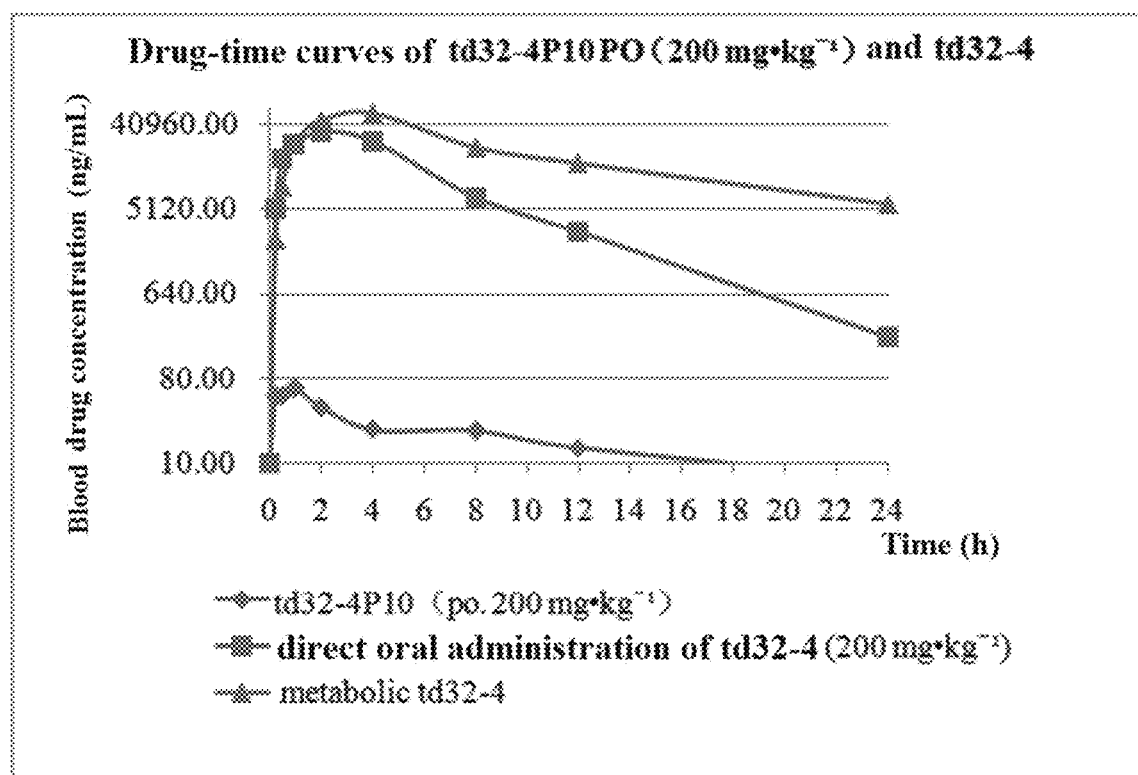
FIG. 5 Blood drug concentration-time curves of td32-4P10, the converted td32-4 in vivo, and td32-4 after oral administration at a dose of 200 mg·kg$^{-1}$.

Compound Td32-4P10 at a High Concentration:

As shown in FIG. 5, when td32-4P10 was orally administered at a dose of 200 mg·kg$^{-1}$, it could be converted into td32-4 in vivo, and the exposure of the converted td32-4 (area under the drug-time curve AUC) was higher than that of orally administered td32-4 at a high dose. Td32-4P10 was almost completely converted into td32-4 within 18 hours in vivo. The oral bioavailability was calculated as F=44.8% according to the exposure of the converted td32-4. (F=18.6% for direct oral administration of td32-4)

The experimental results are summarized as follows (Table 2):

TABLE 2

Oral bioavailability of part of compounds (calculated based on td32-4 in plasma)

| Compd. | F % (10 mpk) | F % (200 mpk) |
| --- | --- | --- |
| td32-4 | 83.4% | 18.6% |
| td32-4P1 | 50.2% | 20.1% |
| td32-4P2 | 45.1% | 15.3% |
| td32-4P3 | 70.2% | 60.1% |
| td32-4P5 | 66.9% | 45.6% |
| td32-4P6 | 71.3% | 55.7% |
| td32-4P9 | 45.1% | 41.9% |
| td32-4P10 | 48.9% | 44.8% |
| td32-4P13 | 48.7% | 19.9% |
| td32-4P19 | 45.1% | 20.0% |
| td32-4P21 | 38.9% | 17.3% |
| td32-4P22 | 41.1% | 21.2% |
| td32-4P23 | 30.8% | 25.1% |
| td32-4P24 | 35.1% | 22.6% |

It can be seen from the pharmacokinetic experimental data of the representative compounds td32-4P3 and td32-4P10 that the compounds according to the present invention can exhibit significantly better in vivo pharmacokinetic properties than td32-4, especially at a high dose (200 mg·kg$^{-1}$), the oral bioavailability was greatly improved, and the plasma concentration of td32-4 was increased. The compounds of the present invention can solve the problem of poor medicinal properties of the compounds such as td32-4 to a certain extent by improving the solubility of such compounds.

Example 27 In Vivo Pharmacodynamic Test

1. Compounds (td32-4, td32-4P3, td32-4P6, td32-4P9, td32-4P10) were selected for in vivo activity evaluation at a single concentration. The animal model was gastric cancer cell MKN45 xenograft model.

Test method: 5×10$^6$ MKN-45 gastric cancer cells were inoculated under the fat pad of the right rib of nude mice, and the tumor formation was observed. Two weeks after the inoculation, the tumor-bearing mice were divided into groups and orally administered with td32-4, td32-4P3, td32-4P6, td32-4P9, and td32-4P10 at a dose of 100 mg·kg$^{-1}$, once a day for 14 days, respectively. Tumor volumes were measured with a caliper and recorded.

Figure 6:
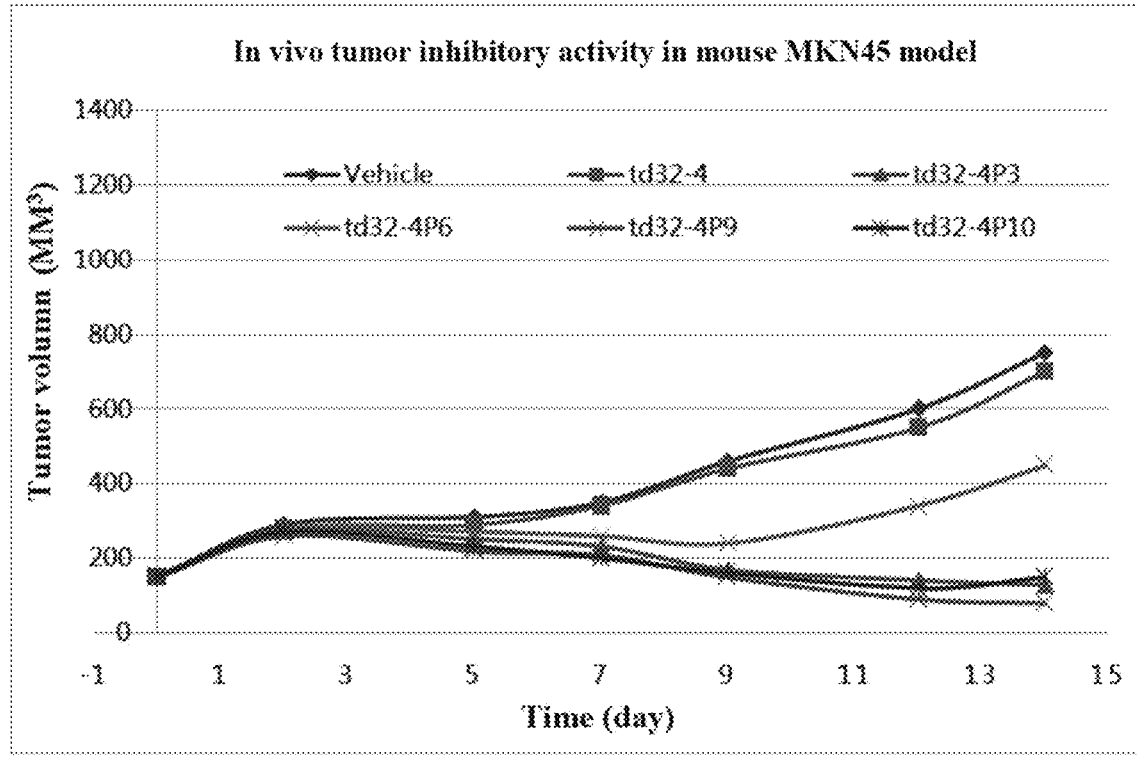
FIG. 6 In vivo tumor inhibitory effects of td32-4P3, td32-4P6, td32-4P9, and td32-4P10 in mice.

The experimental results showed that td32-4P3/9/10 exhibited potent tumor inhibitory effect in nude mouse models. Td32-4P6 exhibited moderate inhibitory activity, while at the same dose, td32-4 did not show significant activity since poor solubility limits the bioavailability. The data results are shown in FIG. 6.

In the present invention, the compound td32-4 is structurally modified by introducing hydrophilic structural fragments, which can significantly improve the water solubility of the compound. Experiments show that the compounds according to the present invention can be converted into td32-4 after oral administration, to exert anti-tumor activity. It is verified by pharmacokinetic experiments that the compounds of the present invention can overcome the inherent defect of poor oral absorption of td32-4; exhibit potent tumor inhibitory activity in tumor-bearing mice and are expected to be developed as novel multi-target antitumor drugs.

Figure 7:
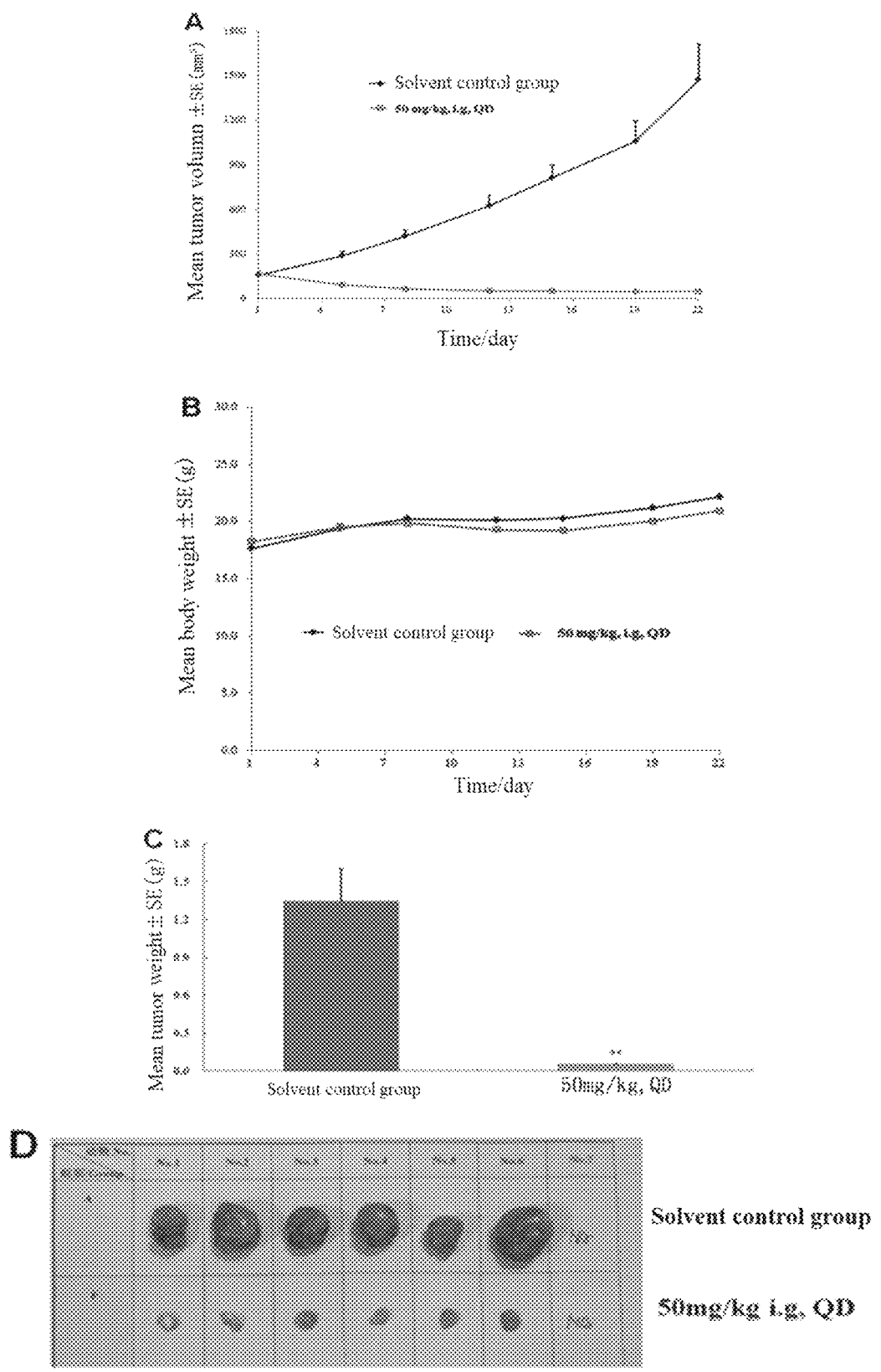
FIG. 7 Tumor inhibitory activity data of td32-4P10 in MV-4-11 nude mouse xenograft model (at a dose of 50 mpk). A) Changes in tumor volume during the administration; B) Changes in body weight of the nude mice caused by the drug during the administration; C) Statistics of tumor weight after completing the administration; D) Tumor anatomical images after completing the administration.
Figure 8:
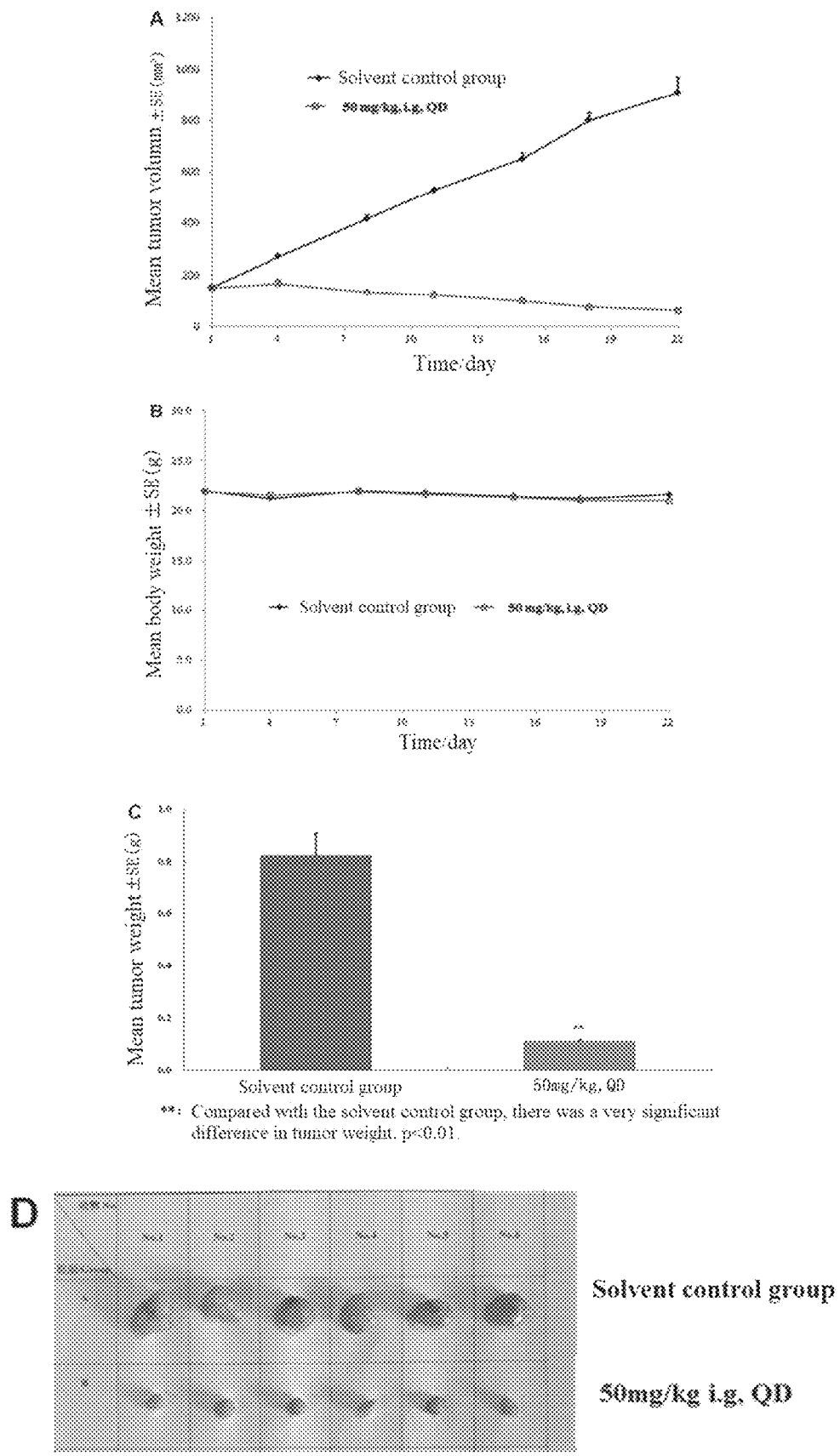
FIG. 8. Tumor inhibitory activity data of td32-4P10 in H358 nude mouse xenograft model (at a dose of 50 mpk). A) Changes in tumor volume during the treatment; B) Changes in body weight of the nude mice caused by the drug during the treatment; C) Count of tumor weight after the treatment; D) Tumor anatomical images after the treatment.
Figure 9:
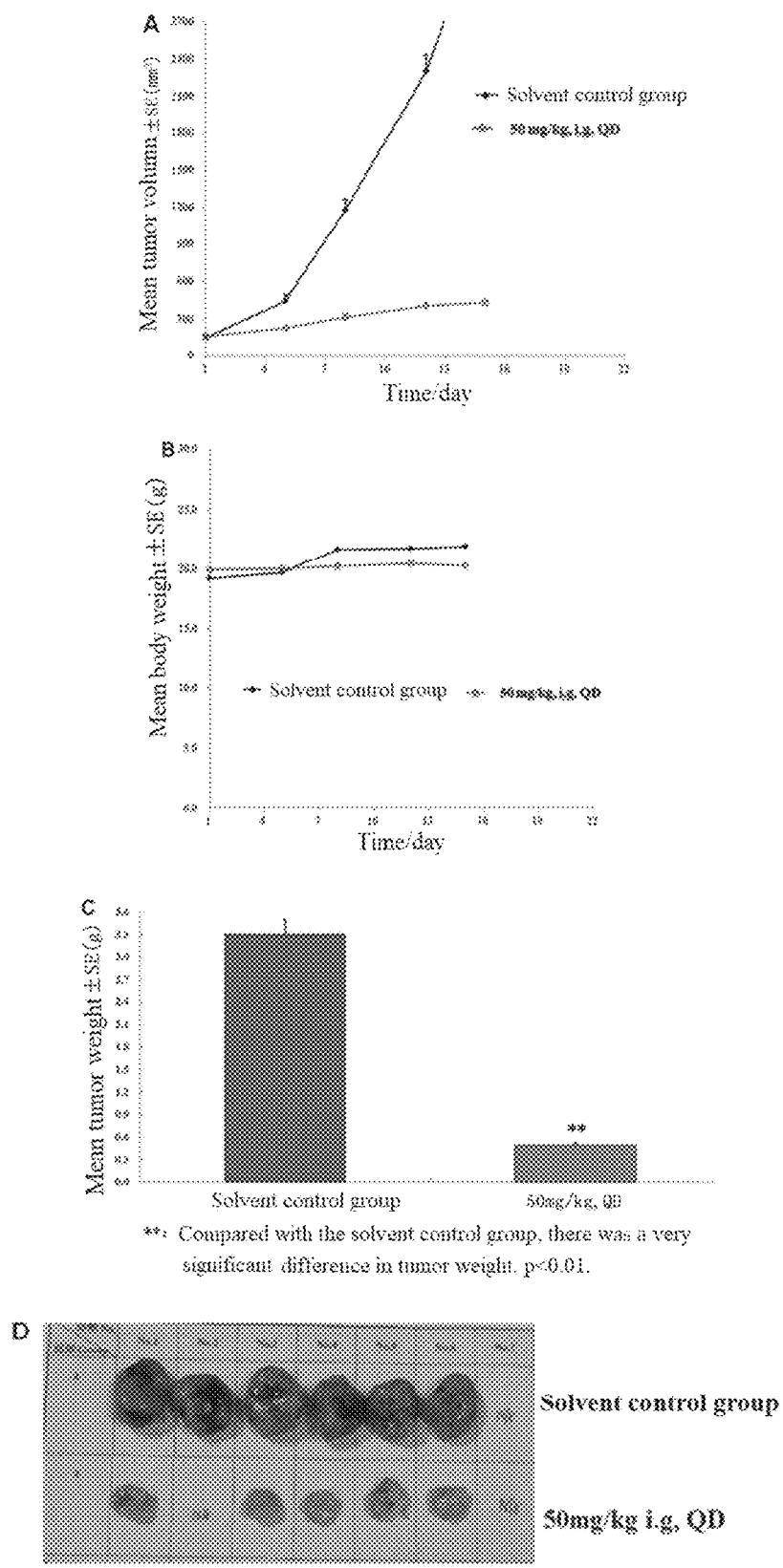
FIG. 9. Tumor inhibitory activity data of td32-4P10 in H82 nude mouse xenograft model (at a dose of 50 mpk). A) Changes in tumor volume during the treatment; B) Changes in body weight of the nude mice caused by the drug during the treatment; C) Count of tumor weight after the treatment; D) Tumor anatomical images after the treatment.

2. The compound td32-4P10 was selected for in vivo activity evaluation. The tumor inhibitory activity data of td32-4P10 were tested in MV-4-11, H358 and H82 nude mouse xenograft model, respectively. The test method is the same as above, and the dose is shown in Table 3. Meanwhile, the changes in tumor volume during the treatment, and the changes in body weight of the nude mice induced by the drug during the treatment were measured. After the treatment, the tumor weights were counted. The tumor anatomical images after the treatment were recorded. The test results are shown in Table 3, FIGS. 7, 8 and 9.

TABLE 3

| | In vivo activity evaluation of Compound td32-4P10 | | | |
|---|---|---|---|---|
| Compound | Xenogeneic model | Dose | T/C (%) | TGI (%) |
| td32-4P10 | MV-4-11 | 50 mg/kg * 21 d, i.g, QD | 3.4% | 109% |
| td32-4P10 | H358 | 50 mg/kg * 21 d, i.g, QD | 6.6% | 112% |
| td32-4P10 | H82 | 50 mg/kg * 14 d, i.g, QD | 11% | 92% |

What is claimed is:

1. A compound or a pharmaceutically acceptable salt, or racemate thereof, wherein the compound has the structure represented by the general formula (I):

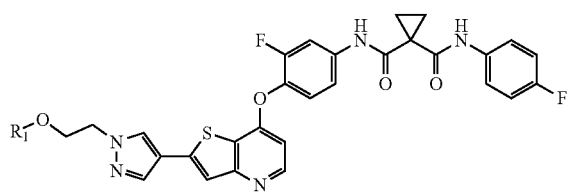

(I)

wherein, $R_1$ is a substituent selected from the group consisting of: carboxyl-substituted $C_3$~$C_8$ alkyl acyl, substituted or unsubstituted phosphonyl,

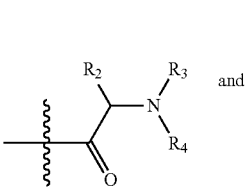 and 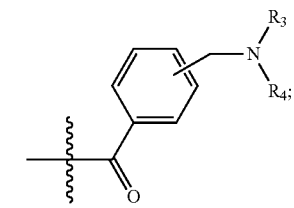

$R_2$ is selected from the group consisting of: hydrogen, halogen, $R_5$-substituted $C_1$~$C_8$ alkyl and $R_5$-substituted $C_6$~$C_{12}$ aryl;

$R_3$, and $R_4$ are independently selected from the group consisting of: hydrogen and $R_5$-substituted $C_1$~$C_6$ alkyl, or $R_3$ and $R_4$ constitute a five- to twelve-membered aliphatic heterocycle;

wherein, $R_5$ is selected from the group consisting of: hydrogen, 1~3 halogens, hydroxyl, $C_1$~$C_6$ alkoxy and $C_6$~$C_{12}$ aryl.

2. The compound of claim 1, wherein:

$R_1$ is selected from the group consisting of: 3-carboxypropionyl, 4-carboxybutanoyl, 5-carboxypentanoyl, 6-carboxyhexanoyl and

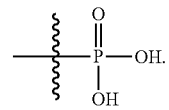

3. The compound of claim 1, wherein:

when $R_1$ is

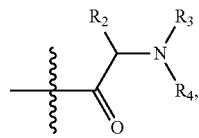

$R_2$ is selected from the group consisting of: hydrogen, halogen, $R_5$-substituted $C_1$~$C_8$ alkyl and $R_5$-substituted $C_6$~$C_{12}$ aryl;

$R_3$ and $R_4$ are independently selected from the group consisting of: hydrogen, and $R_5$-substituted $C_1$~$C_6$ alkyl, or $R_3$ and $R_4$ constitute a five- to twelve-membered aliphatic heterocycle;

wherein, $R_5$ is selected from the group consisting of: hydrogen, 1~3 halogens, hydroxyl, $C_1$~$C_6$ alkoxy or $C_6$~$C_{12}$ aryl.

4. The compound of claim 3, wherein:

when $R_1$=

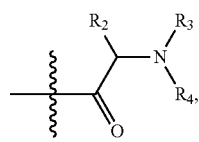

$R_2$ is selected from the group consisting of: hydrogen, fluorine, chlorine, bromine, methyl, —$CH_2F$, —$CHF_2$, —$CF_3$, ethyl, propyl, isopropyl, cyclopropyl, butyl, isobutyl, benzyl, 4-hydroxybenzyl, phenyl and 4-fluorophenyl;

$R_3$, and $R_4$ are independently selected from the group consisting of: hydrogen, methyl, ethyl, 2,2-dimethoxyethyl, propyl and butyl, or $R_3$ and $R_4$ constitute morpholine, piperidine, piperidinylpiperidine or N-methyl piperidine.

5. The compound of claim 3, wherein:
when $R_1=$

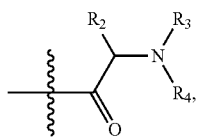

$R_2$ is selected from the group consisting of: hydrogen, methyl, —$CH_2F$, —$CHF_2$, —$CF_3$, ethyl, propyl, isopropyl, isobutyl, benzyl, 4-hydroxybenzyl and phenyl;

$R_3$, and $R_4$ are independently selected from the group consisting of: hydrogen, methyl, ethyl and 2,2-dimethoxyethyl, or $R_3$ and $R_4$ constitute morpholine or N-methylpiperidine.

6. The compound of claim 1, wherein:
when $R_1=$

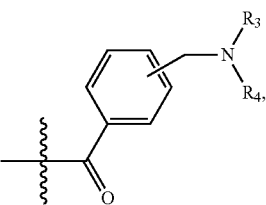

$R_3$, $R_4$ are selected from the following groups: hydrogen, methyl, ethyl, 2,2-dimethoxyethyl, propyl and butyl, or $R_3$ and $R_4$ constitute morpholine, piperidine, piperidinylpiperidine or N-methylpiperidine.

7. The compound of claim 1, having a structure selected from the group consisting of:

| | Structural formula | Chemical formula |
|---|---|---|
| 1 | | $C_{33}H_{27}F_2N_5O_7S$ |
| 2 | | $C_{29}H_{24}F_2N_5O_7PS$ |
| 3 | | $C_{33}H_{30}F_2N_6O_5S$ |
| 4 | | $C_{35}H_{34}F_2N_6O_6S$ |

-continued

| | Structural formula | Chemical formula |
|---|---|---|
| 5 | | $C_{35}H_{32}F_2N_6O_6S$ |
| 6 | | $C_{31}H_{26}F_2N_6O_5S$ |
| 7 | | $C_{32}H_{28}F_2N_6O_5S$ |
| 8 | | $C_{35}H_{34}F_2N_6O_5S$ |
| 9 | | $C_{35}H_{34}F_2N_6O_5S$ |

-continued

| | Structural formula | Chemical formula |
|---|---|---|
| 10 | | $C_{34}H_{32}F_2N_6O_5S$ |
| 12 | | $C_{38}H_{32}F_2N_6O_5S$ |
| 13 | | $C_{34}H_{30}F_2N_6O_5S$ |
| 16 | | $C_{40}H_{33}F_2N_7O_5S$ |
| 17 | | $C_{35}H_{34}F_2N_6O_7S$ |

| | Structural formula | Chemical formula |
|---|---|---|
| 18 | 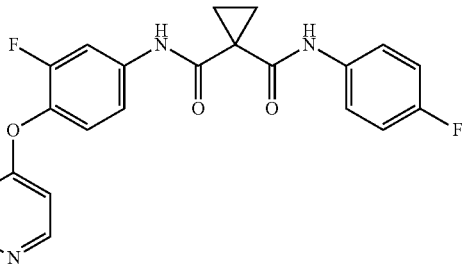 | $C_{34}H_{32}F_2N_6O_5S$ |
| 19 | 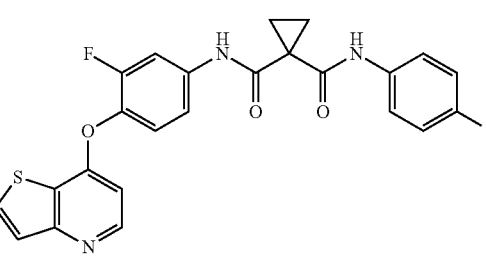 | $C_{41}H_{36}F_2N_6O_6S$ |
| 20 | 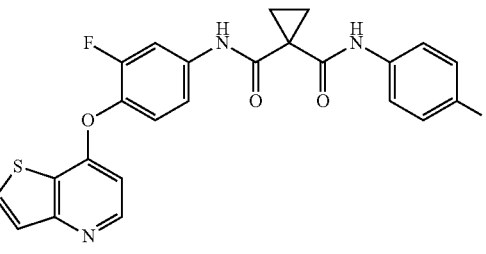 | $C_{41}H_{36}F_2N_6O_6S$ |
| 21 | 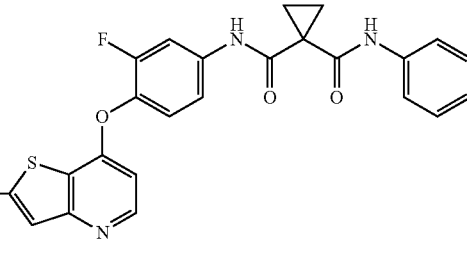 | $C_{42}H_{39}F_2N_7O_5S$ |
| 22 | 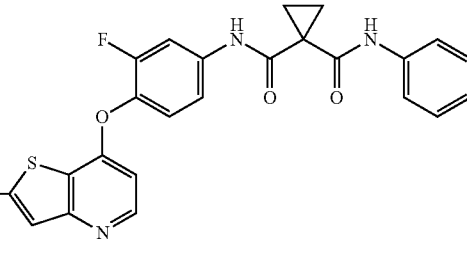 | $C_{42}H_{39}F_2N_7O_5S$ |
| 23 | 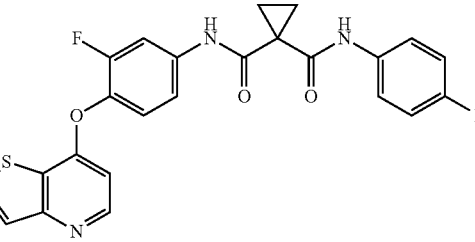 | $C_{41}H_{36}F_2N_6O_5S$ |
and, -continued

| | Structural formula | Chemical formula |
|---|---|---|
| 24 | | $C_{41}H_{36}F_2N_6O_5S$ |

8. A pharmaceutical composition comprising a compound as set forth in claim 1.

9. A method for treating a tumor or a cancer comprising administering to an individual in need thereof a pharmaceutical composition of claim 8.

10. The method of claim 9, wherein the tumor or cancer is a: cervical cancer, seminoma, testicular lymphoma, prostate cancer, ovarian cancer, lung cancer, rectal cancer, breast cancer, skin squamous cell carcinoma, colon cancer, liver cancer, pancreatic cancer, stomach cancer, esophageal cancer, thyroid cancer, bladder transitional epithelial cancer or a leukemia.

11. A method for inhibiting a tyrosine kinase in vivo comprising administering to an individual in need thereof a compound as set forth in claim 1.

12. The method of claim 11, wherein the in vivo administration of the compound treats a tumor or a cancer.

13. The method of claim 12, wherein the tumor or cancer is a: cervical cancer, seminoma, testicular lymphoma, prostate cancer, ovarian cancer, lung cancer, rectal cancer, breast cancer, skin squamous cell carcinoma, colon cancer, liver cancer, pancreatic cancer, stomach cancer, esophageal cancer, thyroid cancer, bladder transitional epithelial cancer or a leukemia.

* * * * *